(12) United States Patent
Sakaguchi et al.

(10) Patent No.: US 7,702,074 B2
(45) Date of Patent: Apr. 20, 2010

(54) X-RAY IMAGING DEVICE AND X-RAY IMAGING METHOD

(75) Inventors: Takuya Sakaguchi, Shioya-gun (JP); Satoru Ohishi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 489 days.

(21) Appl. No.: 11/680,295

(22) Filed: Feb. 28, 2007

(65) Prior Publication Data

US 2007/0206724 A1    Sep. 6, 2007

(30) Foreign Application Priority Data

Mar. 1, 2006    (JP) .............................. 2006-055163

(51) Int. Cl.
  *H05G 1/64* (2006.01)
(52) U.S. Cl. ........................ 378/98.12; 378/4
(58) Field of Classification Search .................. 378/4, 378/15, 98.11, 98.12; 600/425, 431; 382/130, 382/131
See application file for complete search history.

(56) References Cited

U.S. PATENT DOCUMENTS 5,841,830 A * 11/1998 Barni et al. .................... 378/15
6,435,714 B1 * 8/2002 Bruder ........................ 378/196
2002/0191735 A1 12/2002 Strobel
2003/0013953 A1 * 1/2003 Mistretta .................... 600/425
2004/0131156 A1 7/2004 Hebecker et al.
2004/0174960 A1 * 9/2004 Hsieh et al. ................. 378/210
2005/0046644 A1 3/2005 Ohishi

FOREIGN PATENT DOCUMENTS

EP    1 785 092 A1    5/2007
JP    2005-80285    3/2005
WO    WO 03/041583 A2    5/2003

OTHER PUBLICATIONS

Hsieh et al., Fractional scan algorithms for low-dose perfusion CT, 2004, Medical Physics, vol. 31, No. 5, pp. 1254-1257.*
Mori et al., Volumetric Perfusion CT Using Prototype 256-Detector Row CT Scanner: Preliminary Study with Health Porcupine Model, 2005, AJNR Am J Neuroradiol, vol. 26, pp. 2536-2541.*

* cited by examiner

*Primary Examiner*—Chih-cheng G Kao
*Assistant Examiner*—John M Corbett
(74) *Attorney, Agent, or Firm*—Oblon, Spivak, McClelland, Maier & Neustadt, L.L.P.

(57) ABSTRACT

An X-ray generation unit and an X-ray detection unit are controlled by an imaging control unit when two-dimensional images of a sample without a contrast and two-dimensional images of a sample with a contrast are imaged, so as to set imaging angles of these two-dimensional images to be different from each other, and a three-dimensional image of the sample is acquired by an image calculation unit on the basis a plurality of two-dimensional images without a contrast and a plurality of two-dimensional images with a contrast which are acquired under the control of the X-ray generation unit and the X-ray detection unit.

9 Claims, 15 Drawing Sheets

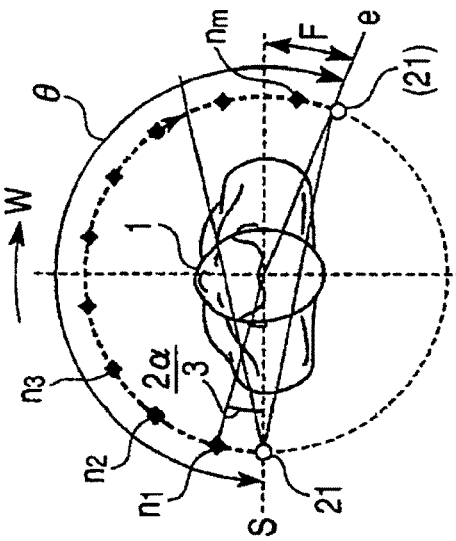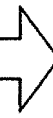
FIG. 5A  FIRST ROTATIONAL ACQUISITION
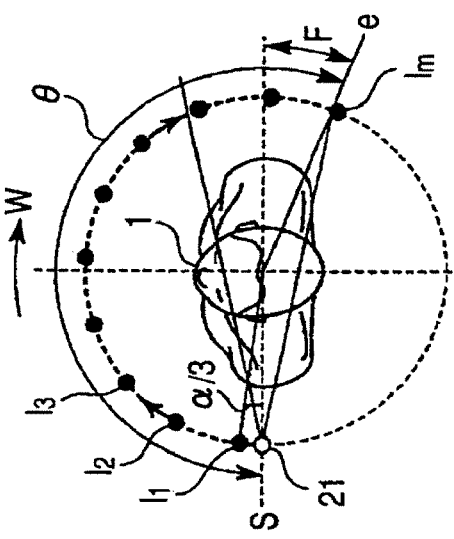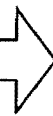
FIG. 5B  SECOND ROTATIONAL ACQUISITION
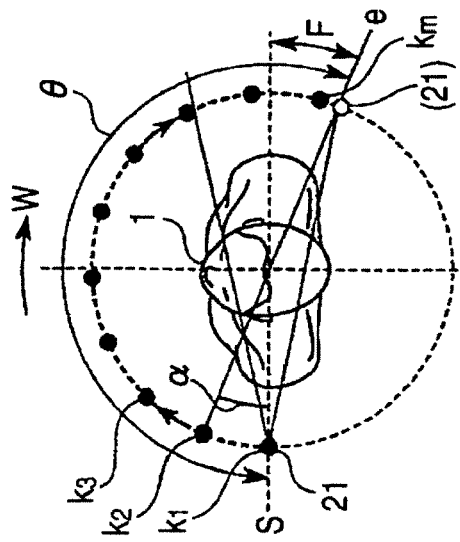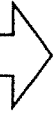
FIG. 5C  THIRD ROTATIONAL ACQUISITION

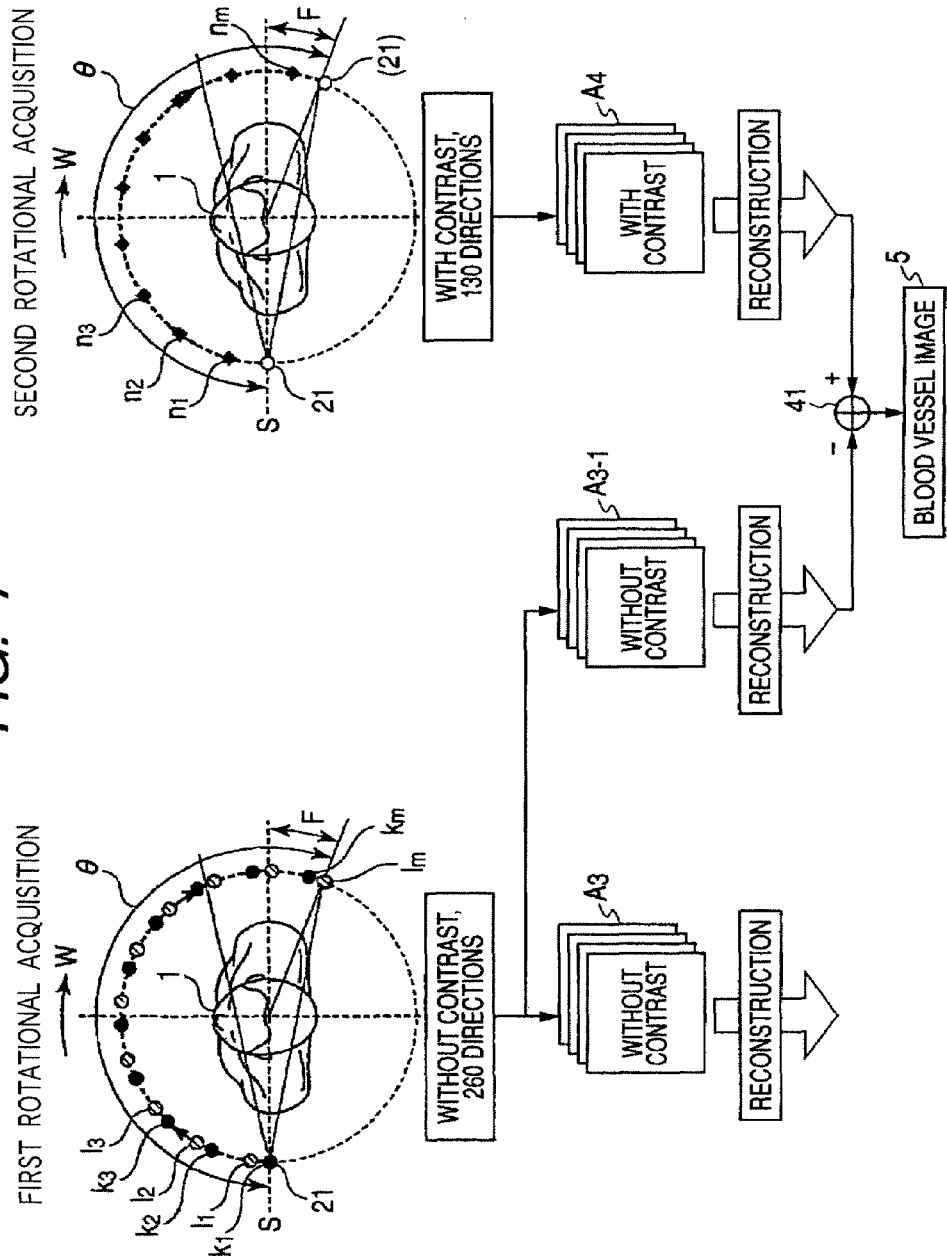

X-RAY IMAGING DEVICE AND X-RAY IMAGING METHOD

CROSS-REFERENCE TO RELATED APPLICATIONS

This application is based upon and claims the benefit of priority from prior Japanese Patent Application No. 2006-055163, filed Mar. 1, 2006, the entire contents of which are incorporated herein by reference.

BACKGROUND OF THE INVENTION

1. Field of the Invention

The present invention relates to an X-ray imaging device and an X-ray imaging method, by which a plurality of two-dimensional images is acquired by performing imaging during the rotation of an X-ray generation unit and an X-ray detection unit around a sample as a rotation center, and a three-dimensional soft tissue image or the like of the sample is acquired by performing a reconstruction of the two-dimensional images.

2. Description of the Related Art

The X-ray imaging device equips a C arm. The C arm is provided with an X-ray generation unit and an X-ray detection unit facing one another. There has been proposed a technique of acquiring a three-dimensional soft tissue image of a sample with the use of the X-ray imaging device. The soft tissue image of the sample acquired according to such technique shows soft tissues of internal organs, etc., inside the sample such as tissues having low X-ray absorption. It has been understood as that the soft tissue image is capable of showing, for example, a difference of a substance X-ray absorption coefficient by 10 H.U. in approximate with a CT value expressed in a relative value from a reference substance.

The X-ray imaging device rotates the X-ray generation unit and the X-ray detection unit around a sample as a rotation center by rotating the C arm. The X-ray imaging device images at every rotary move by predetermined angle while rotating the X-ray generation unit and the X-ray detection unit. The X-ray imaging device acquires a plurality of two-dimensional images by performing the imaging at every rotary movement, and reconstructs a three-dimensional soft tissue image of the sample from the two-dimensional images. For the reconstruction, a three-dimensional soft tissue image is reconstructed by applying the reconstruction theory such as Feldkamp method, or the like. In order to reconstruct the three-dimensional soft tissue image, it is necessary to acquire about 400 frames of two-dimensional images by imaging from about 400 directions of an imaging angle direction.

While surgical operation, the three-dimensional soft tissue image of the sample acquired by the X-ray imaging device is shown on a display. When there is confirmed, for example, a bleeding from vessel, a treatment to stop the bleeding is carried out. In this case, there is a demand to identify a bleeding blood vessel in the sample and observe the blood vessel image and the soft tissue image by overlaying them for a display.

In order to acquire the blood vessel image, it is necessary to inject a contrast agent into a blood vessel and obtain the flow of the contrast agent by an X-ray imaging. For the blood vessel image, as shown in FIG. 17 for example, the rotation of X-ray generation unit and X-ray detection unit is initiated under a condition of without a contrast where the contrast agent is not injected. At this time, the X-ray generation unit and the x-ray detection unit start rotate from a rotation start angle position s to a rotation end angle position e around a sample 1 as a rotation center within the imaging range of θ. The imaging is performed at imaging angle positions $k_1$, $k_2$, ..., $k_n$, respectively, whereat the X-ray generation unit and the X-ray detection unit step each by a predetermined angle. Accordingly, there can be obtained, for example, 400 directions of a two-dimensional image 2 without a contrast. The rotation angle of the imaging range θ is obtained by adding 180° with a Fan angle F. Thus obtained 400 frames of a two-dimensional image 2 without a contrast are recombined to acquire a three-dimensional soft tissue image 3 showing soft tissues.

Alternatively, in the presence of a contrast where the contrasting agent is injected, the X-ray generation unit and the x-ray detection unit are rotated around the sample 1 as a rotation center within the imaging range of θ. Then, the imaging is performed at imaging angle positions $k_1$, $k_2$, ..., $k_n$, respectively, whereat the units step each by predetermined angle as above, thereby obtaining, for example, 400 frames of a two-dimensional image with a contrast.

Next, images 4 which are the subtraction between 400 frames of the two-dimensional image 2 without a contrast and 400 frames of the two-dimensional image 3 with a contrast are obtained. The subtraction images 4 are recombined to acquire a three-dimensional blood vessel image 5 showing blood vessels.

However, since it is necessary to acquire total 800 frames of images, which are 400 frames of a two-dimensional image 2 without a contrast and 400 frames of a two-dimensional image with a contrast, such to acquire the blood vessel image 5, there may be a possibility of increase dose against the sample 1.

An example of the X-ray imaging device is disclosed in JP-A-2005-80285.

BRIEF SUMMARY OF THE INVENTION

It is an object of the invention to provide an X-ray imaging device and a method thereof, by which an image at least showing soft tissues is acquired with the reduced amount of exposure against a sample.

The X-ray imaging device according to the first aspect of the invention includes: an X-ray generation unit which emits X-rays to a sample; an X-ray detection unit which detects the amount of X-rays passing through the sample; an imaging control unit which controls the X-ray generation unit and the X-ray detection unit to differ imaging angles of two-dimensional images from each other at the time of two-dimensionally imaging the sample without a contrast and two-dimensionally imaging the sample with a contrast; and an image calculation unit which acquires a three-dimensional image of the sample on the basis of a plurality of two-dimensional images without a contrast and a plurality of two-dimensional images with a contrast which are obtained under the control of the imaging control unit.

The X-ray imaging device according to the second aspect of the invention includes: an X-ray generation unit which emits X-rays to a sample; an X-ray detection unit which detects the amount of X-rays passing through the sample; an imaging control unit which at least twice rotates the X-ray generation unit and the X-ray detection unit around the sample as a rotation center and images the sample at a plurality of rotation angles different from each other during the rotations; an image calculation unit which acquires a three-dimensional image of the sample by performing a calculation process including at least a reconstruction to the plurality of two-dimensional images which are acquired by performing imaging during the rotations of the X-ray generation unit and the X-ray detection unit.

The X-ray imaging method according to the third aspect of the invention includes: at least twice rotating an X-ray generation unit and an X-ray detection unit around a sample as a rotation center in accordance with a computer processing; imaging the sample at a plurality of rotation angles different from each other during the rotations; acquiring a plurality of two-dimensional images by performing the imaging during the rotations; and acquiring at least a three-dimensional image of the sample by performing a calculation process including at least a reconstruction to the plurality of two-dimensional images.

BRIEF DESCRIPTION OF THE SEVERAL VIEWS OF THE DRAWING

FIG. 5A is a diagram schematically showing a modified example in rotary imaging of the device.

FIG. 5B is a diagram schematically showing a modified example in rotary imaging of the device.

FIG. 5C is a diagram schematically showing a modified example in rotary imaging of the device.

FIG. 7 is a diagram illustrating a method of acquiring a two-dimensional image data in the device.

DETAILED DESCRIPTION OF THE INVENTION

Hereinafter, the first embodiment of the invention will be described with reference to the accompanying drawings.

Figure 1:
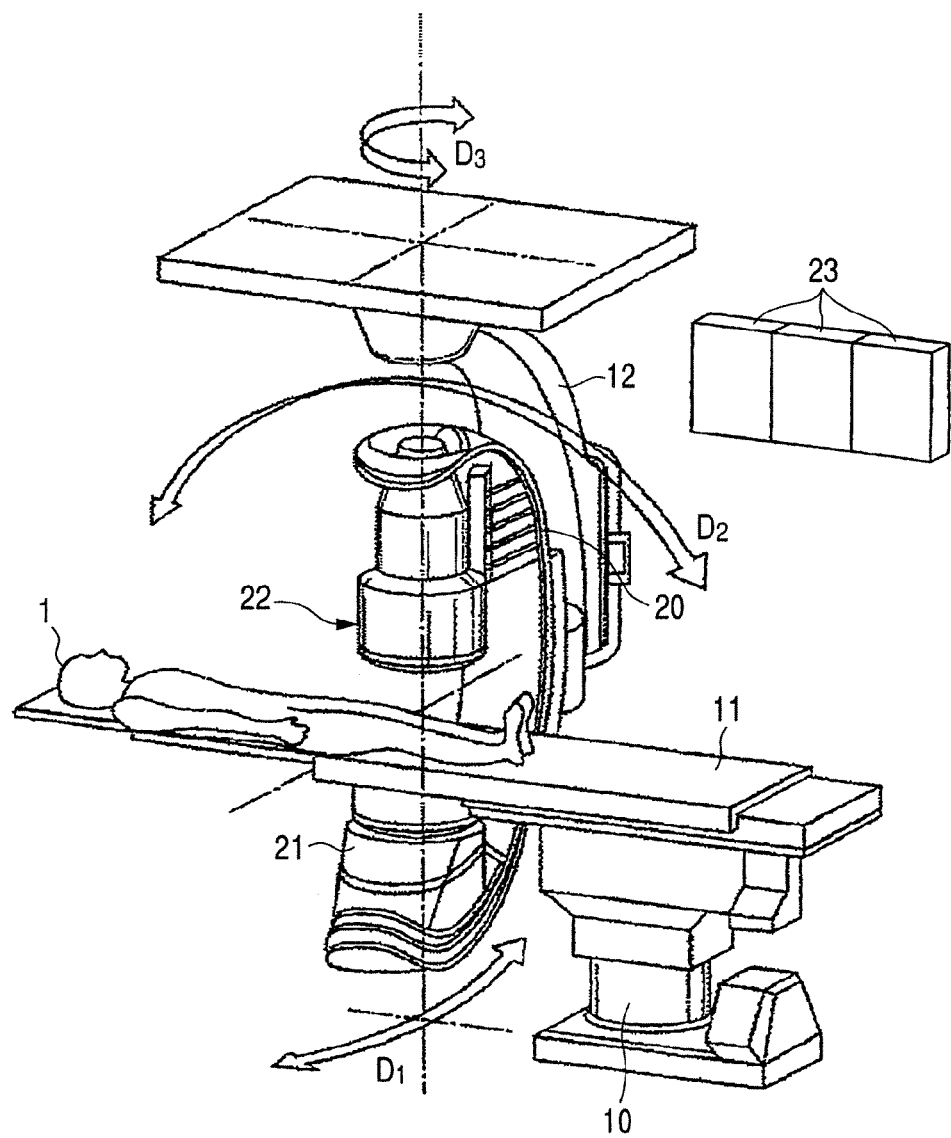
FIG. 1 is a diagram illustrating an outer shape of a first embodiment of an X-ray imaging device according to the invention.

FIG. 1 is a diagram illustrating an overview of an X-ray imaging device. Onto a stand 10, a bed 11 for laying a sample 1 such as patient, etc., is provided. On a ceiling, a support 12 is placed for a C arm 20 to be rotatable. The C arm 20 is capable of rotating in directions $D_1$, $D_2$, and $D_3$ of three orthogonal axes. At each end of the C arm 20, an X-ray generation unit 21 and an X-ray detection unit 22 are provided, respectively, which are facing one another. A plurality of monitors 23 is provided.

The X-ray generation unit 21 equips an X-ray tube. The X-ray generation unit 21 emits an X-ray beam by supplying a voltage and an electric current to the X-ray tube. The X-ray detection unit 22 detects the amount of X-ray beam that is emitted from the X-ray generation unit 21 and passing through the sample 1, and outputs the X-ray image data corresponding to the X-ray detected amount. For the X-ray detection unit 22, a Flat Panel Detector (FPD) or an Image Intensifier (I.I) can be employed.

Figure 2:
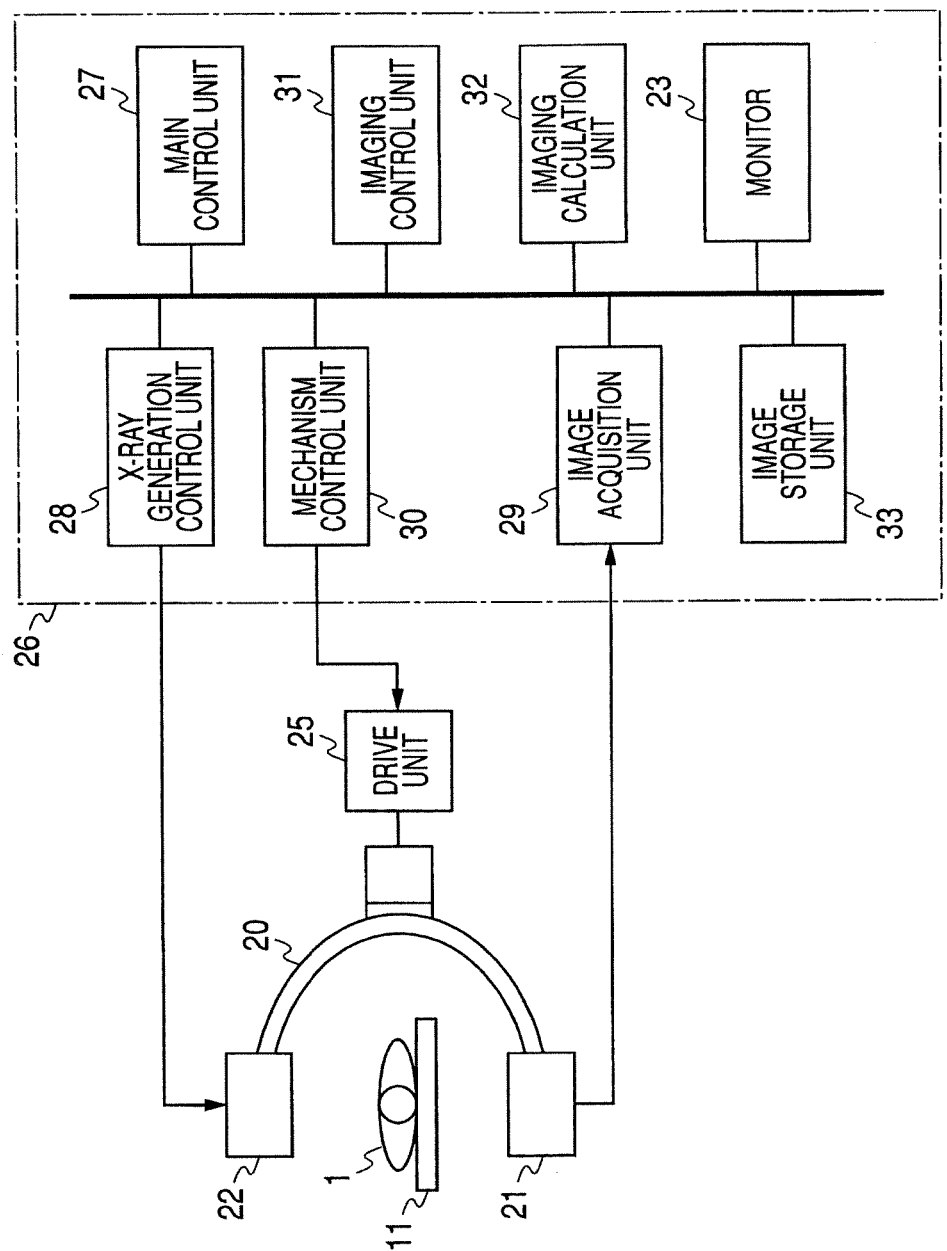
FIG. 2 is a block diagram illustrating a mechanism of the device.

FIG. 2 is a block diagram illustrating a mechanism of the device. The C arm 20 is provided with a drive unit 25. The drive unit 25 rotates the C arm 20. Accordingly, the X-ray generation unit 21 and the X-ray detection unit 22 rotate around the sample 1 as a rotation center.

A calculation processor body 26 is formed with a computer. The calculation processor body 26 performs a series of operation controls including allowing imaging during the rotation of the X-ray generation unit 21 and the X-ray detection unit 22 around the sample 1 as a rotation center by processing an image imaging program preliminarily stored to acquire a plurality of two-dimensional image data, and allowing recombining the two-dimensional image data to acquire a three-dimensional soft tissue image data of the sample 1.

In specific, the calculation processor body 26 operates an X-ray generation control unit 28, an image acquisition unit 29, a mechanism control unit 30, an imaging control unit 31, an imaging calculation unit 32, an image storage unit 33, and the monitor 23, in accordance with each command given from a main control unit 27. The X-ray generation control unit 28 gives a command to the X-ray generation unit 21 to generate the X-ray beam. The command to generate the X-ray beam is given by a voltage value applied to the X-ray tube of the X-ray generation unit 21 or the X-ray condition information instructing a current value.

The image acquisition unit 29 sequentially loads the X-ray image data output from the X-ray detection unit 22, and stores each as a two-dimensional image data into the image storage unit 33.

The mechanism control unit 30 controls the operation of the drive unit 25 rotating the C arm 20. Accordingly, the X-ray generation unit 21 and the X-ray detection unit 22 rotate around the sample 1 as a rotation center.

The imaging control unit 31 gives a command to the mechanism control unit 30 to at least twice rotate the X-ray generation unit 21 and the X-ray detection unit 22 around the sample 1 as a rotation center. At the same time, the imaging control unit 31 gives each command to the X-ray generation control unit 28 and the imaging acquisition unit 29 at every time rotating the X-ray generation unit 21 and the X-ray detection unit 22 for the at least twice rotations. Accordingly, the imaging control unit 31 allows the imaging of the sample 1 at a plurality of rotation angles where angles are deviated to one another.

Figure 3:
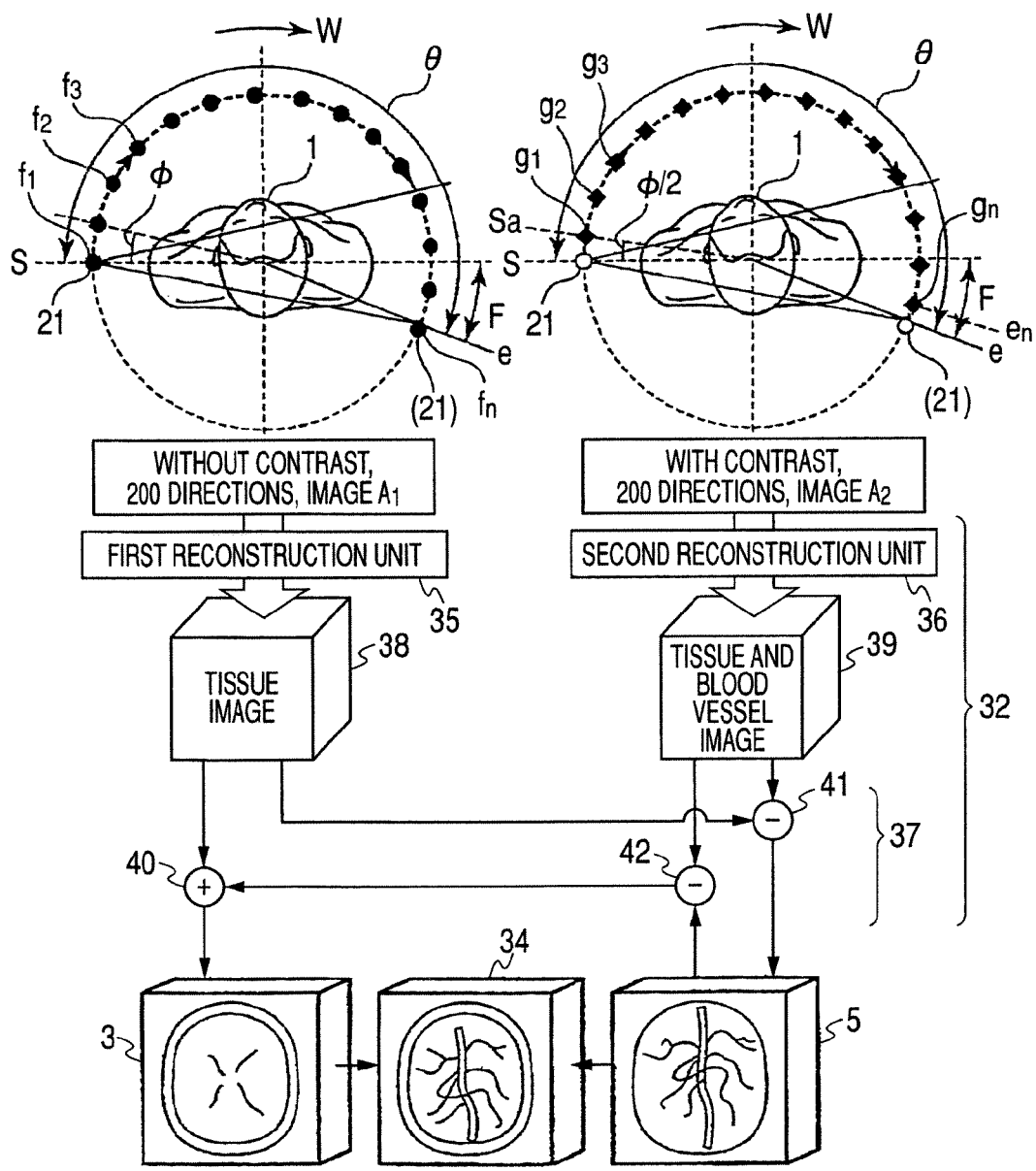
FIG. 3 is a functional block diagram illustrating an image acquisition of the device.

FIG. 3 is a functional block diagram illustrating an image acquisition. The imaging control unit 31 allows the rotation of the X-ray generation unit 21 and the X-ray detection unit 22 around the sample 1 as a rotation center twice without a contrast (contrast agent is not injected to the sample 1) and with a contrast (contrast agent is injected to the sample 1) in the sample 1.

The imaging control unit 31 gives a command to the mechanism control unit 30 to, without a contrast, start the rotation of the X-ray generation unit 21 and the X-ray detection unit 22 around the sample 1 as a rotation center where start rotating from the rotation start angle position S to the rotation end angle position e within the imaging range of θ. At the same time, the imaging control unit 31 gives a command to the X-ray generation control unit 28 and the image acquisition unit 29 to perform imaging at every predetermined φ stepped angles of equal distance, for example, at imaging angle positions $f_1, f_2, \ldots, f_n$, which are stepped by angle φ=1°. The imaging angle direction is, for example, in 200 directions.

The imaging control unit 31 gives a command to the mechanism control unit 30, in the presence of a contrast, to start the rotation of the X-ray generation unit 21 and the X-ray detection unit 22 around the sample 1 as a rotation center where start rotating from the rotation start angle position sa, which is the position deviated by angle φ/2 e.g., deviated by 0.5° angle with respect to the rotation start angle position S, to the rotation end angle position en within the imaging range of θ. The deviated angle φ/2 is set to, for example, a half of the stepped angle φ of imaging angle positions $f_1, f_2, \ldots, f_n$. At the same time, the imaging control unit 31 gives a command to the X-ray generation control unit 28 and the image acquisition unit 29 to perform imaging from the rotation start angle position sa by every predetermined stepped angles of equal distance, for example, at imaging angle positions $g_1, g_2, \ldots, g_n$, which are stepped every by 1° angle. The imaging angle direction in the case of with a contrast is also 200 directions as in the case of without a contrast.

When the X-ray generation unit 21 and the X-ray detection unit 22 are rotated under two conditions of without a contrast and with a contrast, the rotation start angle position S for the case of without a contrast and the rotation start angle position sa for the case of with a contrast differ from each other in response to the deviated angle φ/2. In addition, the rotation end angle position e for the case of without a contrast and the rotation end angle position en for the case of with a contrast also differ in response to the deviated angle φ/2.

The imaging control unit 31 may set the stepped angle for giving equal distant imaging angle positions $f_1, f_2, \ldots, f_n$ in the case of without a contrast, and the stepped angle for giving equal distant imaging angle positions $g_1, g_2, \ldots, g_n$ in the case of with a contrast, to an equal angle of, for example, 1° angle. Accordingly, the imaging control unit 31 deviates the imaging angle positions $f_1, f_2, \ldots, f_n$ for the case of without a contrast to the imaging angle positions $g_1, g_2, \ldots, g_n$ for the case of with a contrast.

The above-mentioned angle φ/2 is set to, for example, a half of the stepped angle φ of imaging angle positions $f_1, f_2, \ldots, f_n$. Accordingly, when imaging angle positions $g_1, g_2, \ldots, g_n$, and imaging angle positions $f_1, f_2, \ldots, f_n$ are combined, imaging angle positions $f_1, g_1, f_2, g_2, \ldots, f_n, g_n$ give an equal angle interval.

The imaging control unit 31 performs the rotation of the X-ray generation unit 21 and the X-ray detection unit 22 in the same plane for rotations of without a contrast and with a contrast.

The X-ray generation unit 21 in FIG. 3 indicates the position at the time of starting the rotation when initiating the X-ray imaging, and the symbol "(21)" in the same figure indicates the position of the X-ray generation unit 21 when terminating the X-ray imaging.

The image calculation unit 32 performs a calculation process such as a reconstruction process and an addition/subtraction process against a plurality of two-dimensional image data acquired by the imaging of with and without a contrast during the rotation of the X-ray generation unit 21 and the X-ray detection unit 22. That is, the image calculation unit 32 subjects the plurality of two-dimensional image data stored in the image storage unit 33 to the calculation process such as a reconstruction process and an addition/subtraction process, and thus acquires a three-dimensional soft tissue image data 3, a three-dimensional blood vessel image data 5, and a three-dimensional soft tissue/blood vessel image data 34, of the sample 1.

In specific, the image calculation unit 32 is provided with a first reconstruction unit 35, a second reconstruction unit 36, and an inter-image calculation unit 37. The first reconstruction unit 35 reads out a plurality of two-dimensional image data, which is acquired by giving no contrast to the sample 1, from the image storage unit 33. The first reconstruction unit 35 allows the reconstruction with the use of the plurality of two-dimensional image data by applying the reconstruction theory such as Feldkamp method, or the like, and acquires a three-dimensional tissue image data 38 of the sample 1. The first reconstruction unit 35 employs, as for the reconstruction filter, a filter such as Shepp & Logan and Ramachandran, which emphasizes a relatively high-frequency component.

The second reconstruction unit 36 allows the reconstruction with the use of the plurality of two-dimensional image data, which is acquired by giving a contrast to the sample 1, by applying the reconstruction theory such as Feldkamp method, or the like, and acquires a three-dimensional soft tissue/blood vessel image data 39 including soft tissues and blood vessels of the sample 1. The second reconstruction unit 36 as in the first reconstruction unit 35 employs, as for the reconstruction filter, a filter such as Shepp & Logan and Ramachandran, which emphasizes a relatively high-frequency component.

The inter-image calculation unit 37 carries out an inter-calculation between the tissue image data 38 reconstructed by the first reconstruction unit 35 and the tissue/blood vessel image data 39 reconstructed by the second reconstruction unit 36, and thus acquires the three-dimensional soft tissue image data 3, the three-dimensional soft tissue/blood vessel image data 34, and the three-dimensional blood vessel image data 5, of the sample 1. In specific, the inter-image calculation unit 37 is provided with an adder 40 and two subtracters 41 and 42. The inter-image calculation unit 37 calculates the difference between the tissue/blood vessel image data 39 and the tissue image data 38 with the subtracter (first calculation unit) 41, and thus acquires the three-dimensional blood vessel image data 5. Next, the inter-image calculation unit 37 calculates the difference between the tissue/blood vessel image data 39 and the blood vessel image data 5 with the subtracter (second calculation unit) 42, and adds the found difference and the tissue image data 38 with the adder (third calculation unit) 40, such to acquire the three-dimensional soft tissue image data 3. Then, the inter-image calculation unit (fourth calculation unit) 37 performs adding the blood vessel image data 5 and the soft tissue image data 3 to acquire the three-dimensional soft tissue/blood vessel image data 34.

Hereinbelow, the imaging operation with the device constructed in the above manner will be explained.

The sample 1 is positioned such to be the rotation center (isocenter) for the X-ray generation unit 21 and the X-ray detection unit 22.

The imaging control unit 31 allows performing the first rotary imaging with the X-ray generation unit 21 and the X-ray detection unit 22 under a condition of without a contrast. That is, the imaging control unit 31 gives a command to the mechanism control unit 30 to start the rotation of the X-ray generation unit 21 and the X-ray detection unit 22 around the sample 1 as a rotation center where start rotating from the rotation start angle position S to the rotation end angle position e within the imaging range of θ. Accordingly, the C arm 20 rotates, for example, in the arrowed W direction. The X-ray generation unit 21 and the X-ray detection unit 22 rotate around the sample 1 as a rotation center. The rotation angle of the imaging range θ is obtained by adding 180° with a Fan angle F. When the performance of the C arm 20 is 50 deg/sec, the C arm 20 requires, for example, about 5 seconds to rotate the imaging range θ.

In addition, the imaging control unit 31 gives a command to the X-ray generation control unit 28 and the image acquisition unit 29 to perform imaging at every predetermined stepped angles of equal distance, for example, at imaging angle positions $f_1, f_2, \ldots, f_n$, which are stepped by 1° angle.

The X-ray generation unit 21 and the X-ray detection unit 22 rotate around the sample 1 as the rotation center where start rotating from the rotation start angle position S to the rotation end angle position e within the imaging range θ. During this rotation, the X-ray generation unit 21 generates an X-ray beam at every predetermined stepped angles of equal distance, for example, at imaging angle positions $f_1, f_2, \ldots, f_n$, which are stepped by 1° angle, which is controlled by the X-ray generation control unit 28. In this case, the imaging angle positions $f_1, f_2, \ldots, f_n$ are, for example, 200 directions.

The X-ray detection unit 22 detects the amount of X-rays passing through the sample 1 at imaging angle positions $f_1, f_2, \ldots, f_n$, and outputs its X-ray image data. The rotation angle of the imaging range 0 is obtained by adding 180° with a Fan angle F.

As a result, the image acquisition unit 29 sequentially loads the X-ray image data output from the X-ray detection unit 22, and stores in the image storage unit 33, for example, as 200 frames of two-dimensional image data (Mask image data) $A_1$ without a contrast.

When the first rotary imaging is finished, the C arm 20 returns back to its original position.

Next, the imaging control unit 31 allows performing the second rotary imaging with the X-ray generation unit 21 and the X-ray detection unit 22 under a condition of with a contrast. That is, the imaging control unit 31 gives a command to the mechanism control unit 30 to start the rotation from the rotation start angle position sa, which is the position deviated by angle φ/2, half of the stepped angle φ (=1°) of imaging angle positions $f_1, f_2, \ldots, fn$, e.g., deviated by φ=0.5° with respect to the rotation start angle position S for the case of without a contrast, to the rotation end angle position en within the imaging range of θ.

Accordingly, the C arm 20 rotates, for example, in the arrowed W direction. The X-ray generation unit 21 and the X-ray detection unit 22 rotate around the sample 1 as a rotation center (isocenter). The rotations of with and without a contrast with the X-ray generation unit 21 and the X-ray detection unit 22 are performed in the same plane.

In addition, the imaging control unit 31 gives a command to the X-ray generation control unit 28 and the image acquisition unit 29 to perform imaging from the rotation start angle position sa by every predetermined stepped angles of equal distance, for example, at imaging angle positions $g_1, g_2, \ldots, g_n$, which are stepped by 1° angle as in the case of without a contrast. The imaging angle direction in the presence of a contrast is also 200 directions as in the case of without a contrast.

The X-ray generation unit 21 and the X-ray detection unit 22 rotate around the sample 1 as the rotation center where start rotating from the rotation start angle position sa to the rotation end angle position en within the imaging range θ. During this rotation of the X-ray generation unit 21 and the X-ray detection unit 22, the X-ray generation unit 21 generates an X-ray beam at every predetermined stepped angles of equal distance, for example, at imaging angle positions $g_1, g_2, \ldots, g_n$, which are stepped by 1° angle, which is controlled by the X-ray generation control unit 28. The imaging angle positions $g_1, g_2, \ldots, g_n$ are, for example, 200 directions. The X-ray detection unit 22 detects the amount of X-rays passing through the sample 1 at imaging angle positions $g_1, g_2, \ldots, g_n$, and outputs its X-ray image data. As a result, the image acquisition unit 29 sequentially loads the X-ray image data outputted from the X-ray detection unit 22. Then, the image acquisition unit 29 stores in the image storage unit 33, for example, as 200 frames of two-dimensional image data (Contrast image data) $A_2$ with a contrast.

The image storage unit 33 stores 400 frames of two-dimensional image data in total obtained from 200 frames of the two-dimensional image data $A_1$ without a contrast and 200 frames of the two-dimensional image data $A_2$ with a contrast. Each of two dimensional image data $A_1$ without a contrast and $A_2$ with a contrast, is obtained by performing imaging at imaging angle positions $f_1, f_2, \ldots, f_n$ and at imaging angle positions $g_1, g_2, \ldots, g_n$, respectively, which are deviated by angle φ e.g., deviated by 0.5° angle.

Accordingly, 400 frames of the two-dimensional image data $A_1$ and $A_2$ in total are same to the images acquired at imaging angle positions $f_1, g_1, f_2, g_2, \ldots, f_n, g_n$, of equal interval. The two-dimensional image data $A_1$ and $A_2$ have the same information as the ones obtained by taking the image of organs in the sample 1 at imaging angles of 400 directions. When there are two-dimensional image data of 400 imaging directions, the soft tissue image of the sample 1 can be obtained. When there are two-dimensional image data of 200 imaging directions, the blood vessel image of the sample 1 can be obtained.

The first reconstruction unit 35 reads out, for example, 200 frames of the two-dimensional image data $A_1$ stored in the image storage unit 33. The first reconstruction unit 35 allows the reconstruction with the use of two-dimensional image data $A_1$, and acquires the three-dimensional tissue image data 38 of the sample 1. The first reconstruction unit 35 may conduct the reconstruction at the same time of acquiring the two-dimensional image data $A_2$ with a contrast without waiting for the acquisition of the two-dimensional image data $A_2$ with a contrast to end.

The second reconstruction unit 36 allows the reconstruction with the use of, for example, 200 frames of the two-dimensional image data $A_2$ acquired by giving a contrast to the sample 1, and acquires the three-dimensional tissue/blood vessel image data 39 including soft tissues and blood vessels of the sample 1.

The inter-image calculation unit 37 calculates the difference between the tissue/blood vessel image data 39 and the tissue image data 38 with the subtracter 41, and thus acquires the three-dimensional blood vessel image data 5. The three-dimensional blood vessel image data 5 only shows blood vessels.

Next, the inter-image calculation unit 37 calculates the difference between the tissue/blood vessel image data 39 and the blood vessel image data 5 with the subtracter 42, and adds the found difference and the tissue image data 38 with the adder 40, such to acquire the three-dimensional soft tissue image data 3.

Subsequently, the inter-image calculation unit 37 performs adding the blood vessel image data 5 and the soft tissue image data 3 to acquire the three-dimensional soft tissue/blood vessel image data 34.

As a result, the blood vessel image data 5, the soft tissue image data 3, and the soft tissue/blood vessel image data 34 of the sample 1 are displayed on the monitor 23.

According to the first embodiment as above, the X-ray generation unit 21 and the X-ray detection unit 22 are rotated under a condition of without a contrast from the rotation start angle position S and the imaging is performed at imaging angle positions $f_1, f_2, \ldots, f_n$, respectively, thereby acquiring, for example, 200 frames of the two-dimensional image data $A_1$ without a contrast. In addition, the X-ray generation unit 21 and the X-ray detection unit 22 are rotated under a condition of with a contrast from the rotation start angle position sa, which is the position deviated by angle φ e.g., deviated by 0.5° angle with respect to the rotation start angle position S, and the imaging is performed at imaging angle positions $g_1, g_2, \ldots, g_n$, respectively, thereby acquiring, for example, 200 frames of the two-dimensional image data $A_2$ with a contrast. The total 400 frames of the two-dimensional image data $A_1$ without a contrast and $A_2$ with a contrast have the same information as the ones obtained by taking the image of organs in the sample 1 at imaging angles of 400 directions. When there are two-dimensional image data of 400 imaging directions, the soft tissue image of the sample 1 can be obtained. When there are two-dimensional image data of 200 imaging directions, the blood vessel image of the sample 1 can be obtained. Accordingly, from the reconstruction with the use of each 200 frames of the two-dimensional image data $A_1$ without a contrast and $A_2$ with a contrast and the addition/subtraction calculation, the three-dimensional blood vessel image data 5, the three-dimensional soft tissue image data 3, and the three-dimensional soft tissue/blood vessel image data 34, of the sample 1 are acquired.

As a result, only by performing the imaging of total 400 frames of 200 imaging without a contrast and 200 imaging with a contrast, the three-dimensional soft tissue image data 3, the blood vessel image data 5, and the soft tissue/blood vessel image data 34, of the sample 1 can be acquired. In this manner, the amount of X-ray exposure against the sample 1 can be reduced.

Reduced number of frames of imaging can also reduce the imaging time. Thus, the technique can be more swiftly done. In addition, the risk of obtaining a low quality image due to the move of the sample 1 e.g., patient during perform imaging can be reduced by half when the imaging time is shortened.

While subjecting the sample 1 to an operation, the three-dimensional soft tissue image of the sample 1 acquired by the X-ray imaging device is displayed on the monitor 23. When there is confirmed, for example, a bleeding in the sample 1 while observing the soft tissue image displayed on the monitor 23, a treatment to stop the bleeding is carried out. In this case, the operator may give a request to identify a bleeding blood vessel in the sample 1 and display the soft tissue/blood vessel image data 34 obtained by superimposing the blood vessel image data 5 and the soft tissue image data 3 on the monitor 23. The present device allows the display of the soft tissue/blood vessel image data 34 on the monitor 23, thereby meeting the request from the operator.

Next, the second embodiment of the invention will be described with reference to the accompanying drawings. Since the device shown in FIG. 1 and FIG. 2 has a same configuration, a description thereof will be omitted.

Figure 4:
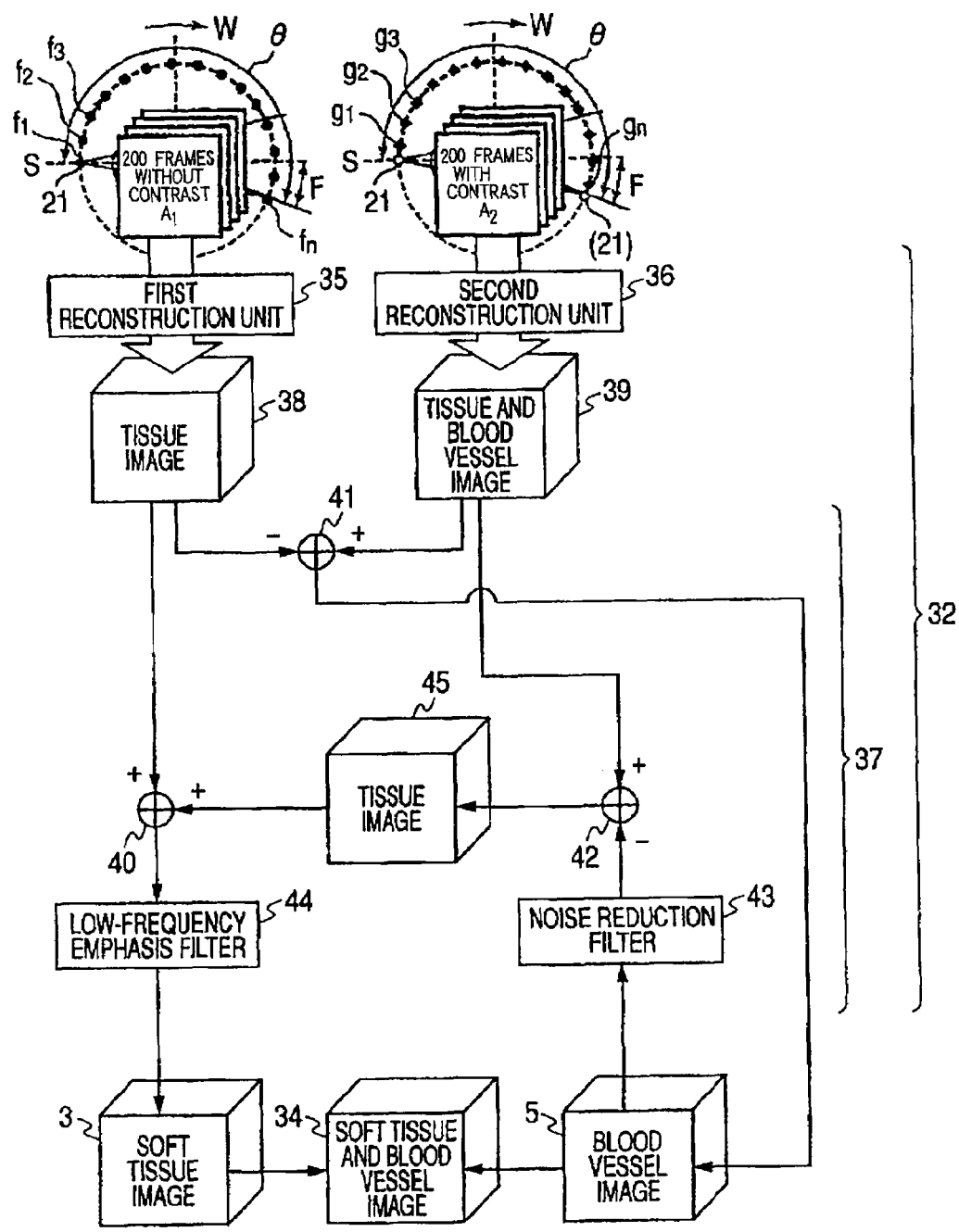
FIG. 4 is a functional block diagram illustrating an image acquisition in a second embodiment of an X-ray imaging device according to the invention.

FIG. 4 is a functional block diagram illustrating an image acquisition of an X-ray imaging device, and particularly shows a specific configuration of the inter-image calculation unit 37. The inter-calculation unit 37 is provided with a noise reduction filter 43 and a low-frequency emphasis filter 44. The noise reduction filter 43 reduces a noise included in the blood vessel image 5. The noise reduction filter 43, for example, employs a median filter. The noise reduction filter 43 is not limited by the median filter, and various noise reduction filters can also be employed.

The low-frequency emphasis filter 44 emphasizes a low-frequency component included in the three-dimensional soft tissue image data 3 outputted from the adder 40. In specific, the low-frequency emphasis filter 44 emphasizes a low-frequency component with the use of a relatively strong low-frequency emphasis filter for the body axis direction, and emphasizes a low-frequency component with the use of a relatively weak low-frequency emphasis filter for the Axial direction (cross section which is perpendicular to the body axis), in the soft tissue image data 3.

Hereinbelow, the imaging operation with the device constructed in the above manner will be explained.

As above, the imaging is performed at imaging angle positions $f_1, f_2, \ldots, f_n$. Accordingly, 200 frames of the two-dimensional image data $A_1$ without a contrast are acquired. Each imaging is performed at imaging angle positions $g_1, g_2, \ldots, g_n$. Accordingly, 200 frames of the two-dimensional image data $A_2$ with a contrast are acquired.

The first reconstruction unit 35 reads out, for example, 200 frames of the two-dimensional image data $A_1$ stored in the image storage unit 33, and allows the reconstruction with the use of two-dimensional image data $A_1$, thereby acquiring the three-dimensional tissue image data 38 of the sample 1.

The second reconstruction unit 36 allows the reconstruction with the use of, for example, 200 frames of the two-dimensional image data $A_2$ acquired by giving a contrast to the sample 1, and acquires the three-dimensional tissue/blood vessel image data 39 including soft tissues and blood vessels of the sample 1.

The inter-image calculation unit 37 calculates the difference between the tissue/blood vessel image data 39 and the tissue image data 38 with the subtracter 41, and thus acquires the three-dimensional blood vessel image data 5. The blood vessel image data 5 has many noise components in the region other than the blood vessels. Thus, the noise reduction filter 43 reduces the noise component included in the blood vessel image data 5.

Next, the inter-image calculation unit 37 calculates the difference between the tissue/blood vessel image data 39 and the blood vessel image data 5 which has been subjected to the noise component reduction, with the subtracter 42, and acquires the tissue image data 45 showing tissues in the sample 1. The tissue image data 38 and the tissue image data 45 have information obtained from different imaging directions of imaging angle directions $f_1, f_2, \ldots, f_n$, and imaging angle positions $g_1, g_2, \ldots, g_n$, respectively. When the tissue image data 38 and the tissue image data 45 are added, a density resolution which can express soft tissues can be obtained.

The inter-image calculation unit 37 adds the tissue image data 38 and the tissue image data 45 with the adder 40, and thus acquires the three-dimensional soft tissue image data 3. In addition, the low-frequency emphasis filter 44 emphasizes a low-frequency component with the use of a relatively strong low-frequency emphasis filter for the body axis direction, and emphasizes a low-frequency component with the use of a relatively weak low-frequency emphasis filter for the Axial direction, in the soft tissue image data 3.

The inter-image calculation unit 37 adds the blood vessel image data 5 and the soft tissue image data 3 to acquire the three-dimensional soft tissue/blood vessel image data 34. These blood vessel image data 5, the soft tissue image data 3, and the soft tissue/blood vessel image data 34, of the sample 1, are displayed on the monitor 23.

According to the above-mentioned second embodiment, the blood vessel image data 5 for which the noise component is reduced, the soft tissue image data 3, and the soft tissue/blood vessel image data 34 can be acquired as well as achieving the same effect as in the first embodiment.

The first and the second embodiments may also be modified as follows.

In the first and the second embodiments, the imaging in the presence of a contrast is performed after performing the imaging without a contrast, but the imaging in the presence of a contrast may be performed before performing the imaging without a contrast. The contrast may be given by intra arterial injection or intravenous injection. After performing the imaging without a contrast, the imaging without a contrast may be re-performed.

The number of imaging frames is mentioned as 200 frames without a contrast and 200 frames with a contrast, but may not be limited by this and may be changed to the number necessary for the examination, for example, 210 frames without a contrast and 210 frames with a contrast.

The imaging is performed twice by performing the first rotary imaging without a contrast and the second rotary imaging with a contrast, but three or more rotary imaging may be performed in combination.

FIG. 5A to FIG. 5C show one example of first to third rotary imaging. For the first rotary imaging shown in FIG. 5A, the imaging control unit 31 allows the rotation of the X-ray generation unit 21 and the X-ray detection unit 22 around the sample 1 as a rotation center under a condition of without a contrast, where start rotating from the rotation start angle position S to the rotation end angle position e within the imaging range of θ, and allows performing the imaging at every predetermined α stepped angles of equal distance such as at imaging angle positions $k_1, k_2, \ldots, k_m$. In this case, the imaging angle positions $k_1, k_2, \ldots, k_m$, for example, are 130 directions.

For the second rotary imaging shown in FIG. 5B, the imaging control unit 31 allows performing the imaging without a contrast at imaging angle positions $l_1, l_2, \ldots, l_n$, which are the position deviated by ⅓ of the angle α, angle (α/3), with respect to the rotation start angle position S for the case of without a contrast. In this case, the imaging angle positions $l_1, l_2, \ldots, l_m$, for example, are 130 directions.

For the third rotary imaging shown in FIG. 5C, the imaging control unit 31 allows performing the imaging without a contrast at imaging angle positions $n_1, n_2, \ldots, n_n$, which are the position deviated by ⅔ of the angle α, angle (2α/3), with respect to the rotation start angle position S for the case of without a contrast. In this case, the imaging angle positions $n_1, n_2, \ldots, n_m$, for example, are 130 directions.

As a result, 260 frames without a contrast and 130 frames with a contrast can be acquired. A plurality of two-dimensional image data acquired by the first to third rotary imaging is obtained at equal distant imaging angle positions $k_1, l_1, n_1, k_2, l_2, n_2, \ldots, k_m, l_m, n_m$.

Figure 6A:
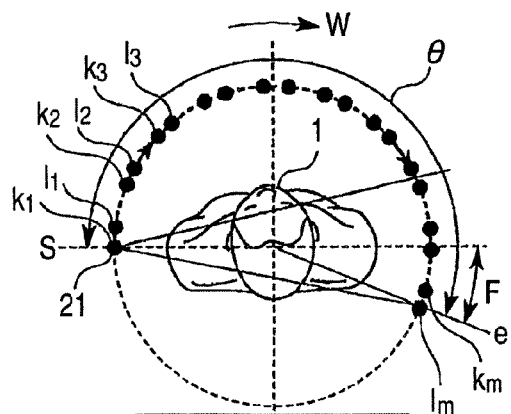
FIG. 6A is a diagram schematically showing a modified example in rotary imaging of the device.
Figure 6B:
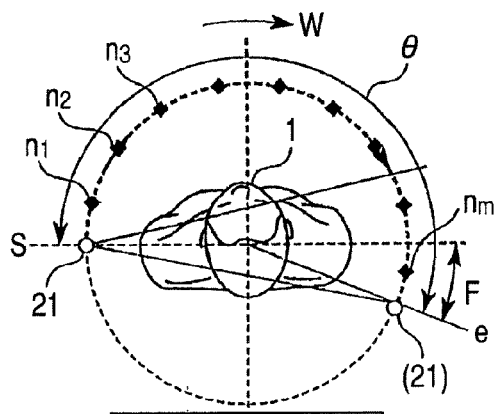
FIG. 6B is a diagram schematically showing a modified example in rotary imaging of the device.

FIG. 6A and FIG. 6B show rotary imaging which is performed by combining the first and the second rotary imaging shown in FIG. 5A and FIG. 5B. For the first rotary imaging shown in FIG. 6A, the imaging control unit 31 allows the rotation of the X-ray generation unit 21 and the X-ray detection unit 22 around the sample 1 as a rotation center under a condition of without a contrast, where start rotating from the rotation start angle position S to the rotation end angle position e within the imaging range of θ. The imaging control unit 31 allows performing the imaging at imaging angle positions $k_1, l_1, k_2, l_2, \ldots, k_m, l_m$, which are at angle of irregular distance, during the rotation of the X-ray generation unit 21 and the X-ray detection unit 22. The imaging angle positions $k_1, l_1, k_2, l_2, \ldots, k_m, l_m$, for example, are 260 directions. The imaging angle positions $k_1, l_1, k_2, l_2, \ldots, k_m, l_m$ are distant at irregular interval but the imaging angle positions $k_1$ and $l_1$, $k_2$ and $l_2, \ldots, k_m$ and $l_m$, are deviated by angle (α/3), respectively. The imaging angle positions $l_1$ and $k_2$, $l_2$ and $k_3, \ldots, l_{m-1}$ and $k_m$, are deviated by angle (2α/3), respectively.

FIG. 6B shows a second rotary imaging. For the second rotary imaging, the imaging control unit 31 allows performing the imaging with a contrast at imaging angle positions $n_1, n_2, \ldots, n_m$, which are the position deviated by ⅔ of the angle α, angle (2α/3), with respect to the rotation start angle position S for the case of without a contrast. The imaging angle positions $n_1, n_2, \ldots, n_m$, for example, are 130 directions.

As a result, 260 frames of the two-dimensional image data without a contrast can be acquired. Also, 130 frames of the two-dimensional image data with a contrast can be acquired. A plurality of two-dimensional image data acquired by the first and second rotary imaging is obtained at equal distant imaging angle positions $k_1, l_1, n_1, k_2, l_2, n_2, \ldots, k_m, l_m, n_m$.

Hereat, the first reconstruction unit 35 allows the reconstruction with the use of, for example, 260 frames of the two-dimensional image data obtained from the imaging at imaging angle positions $k_1, l_1, k_2, l_2, \ldots, k_m, l_m$, of irregular interval so as to acquire the three-dimensional tissue image data of the sample 1. In the reconstruction, a correction is conducted to prevent the generation of an artifact.

FIG. 7 shows a method of acquiring a two-dimensional image data. Herein, same symbols are given to the same parts as in FIG. 6A and FIG. 6B, and a detailed description thereof will be omitted. For the first rotary imaging, the imaging is performed under a condition of without a contrast at imaging angle positions $k_1, l_1, k_2, l_2, \ldots, k_m, l_m$. Accordingly, 260 frames of the two-dimensional image data $A_3$ without a contrast are acquired. From the first rotary imaging, without being limited to acquiring 260 frames of the two-dimensional image data $A_3$, many of two-dimensional image data may also be acquired by performing the imaging at many imaging angle positions of narrower interval than the imaging interval of imaging angle positions $k_1, l_2, k_2, l_2, \ldots, k_m, l_m$.

For the second rotary imaging, the imaging is performed under a condition of with a contrast at imaging angle positions $n_1, n_2, \ldots, n_m$. Accordingly, 130 frames of the two-dimensional image data $A_4$ with a contrast are acquired.

The first reconstruction unit 35 extracts a two-dimensional image data $A_{3-1}$, for example, from 260 frames of the two-dimensional image data $A_3$ without a contrast. The extracted two-dimensional image data $A_{3-1}$ is combined with, for example, 130 frames of the two-dimensional image data $A_4$ with a contrast, and as a result, an image data with imaging angle positions of equal interval is obtained.

The first reconstruction unit 35 allows the reconstruction with the use of the extracted two-dimensional image data $A_{3-1}$, and acquires the three-dimensional tissue image data 38 of the sample 1. The second reconstruction unit 36 allows the reconstruction with the use of, for example, 130 frames of the two-dimensional image data $A_4$ acquired by giving a contrast to the sample 1, and acquires the three-dimensional tissue/blood vessel image data 39 including tissues and blood vessels of the sample 1. The subtracter 41 calculates the difference between the tissue/blood vessel image data 39 and the tissue image data 38, and acquires the three-dimensional blood vessel image data 5. The calculation process of the image calculation unit 32 is same as above, thus the description thereof will be omitted.

According to the first and the second embodiments, the X-ray generation unit 21 and the X-ray detection unit 22 rotated by the C arm 20 are all rotated in the arrowed W direction for the first to third rotary imaging. In this manner, it is easy to mechanically determine the position for the X-ray generation unit 21 and the X-ray detection unit 22 by the C arm 20, etc.

Figure 8:
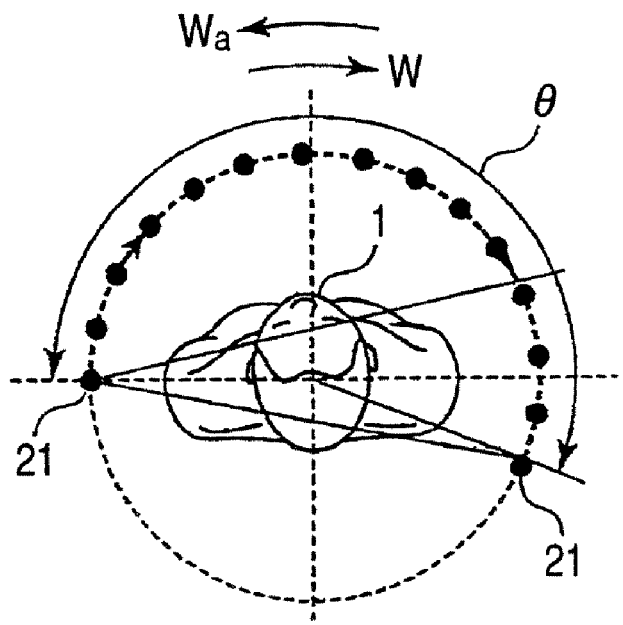
FIG. 8 is a diagram illustrating a modified example of a rotation direction of an X-ray generation unit and an X-ray detection unit in the device.

The rotation of the X-ray generation unit 21 and the X-ray detection unit 22 may be a reciprocal movement of, for example, rotating in the arrowed W direction for the first rotary imaging and rotating in the Wa direction which is opposite to the arrowed W direction for the second rotary imaging, as shown in FIG. 8. In this manner, a total time taken for rotating the X-ray generation unit 21 and the X-ray detection unit 22 by the C arm 20 in the first and the second rotary imaging can be reduced.

Figure 9:
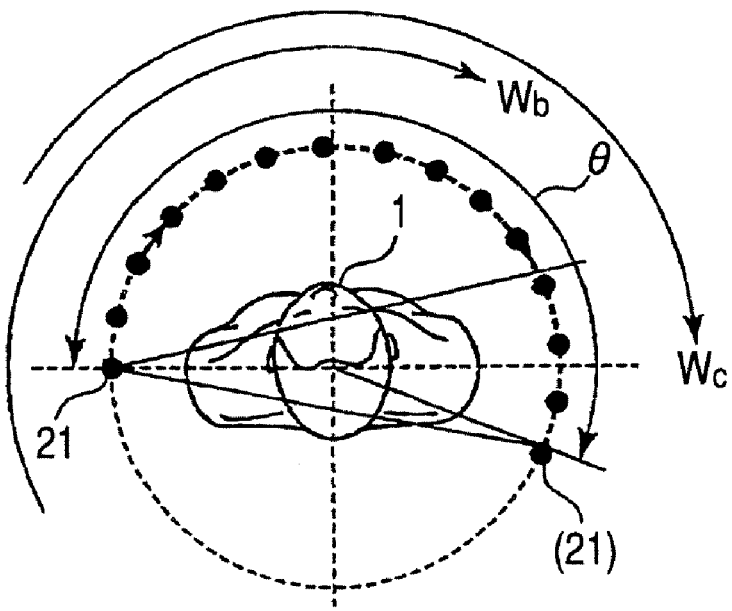
FIG. 9 is a diagram illustrating a modified example of a rotation direction of the X-ray generation unit and the X-ray detection unit in the device.

The rotation of the X-ray generation unit 21 and the X-ray detection unit 22 may be, for example, performed in the arrowed Wb direction by 200° for the first rotary imaging and in the arrowed Wc direction by 200° for the second rotary imaging, as shown in FIG. 9. Herein, the first rotary imaging is in the condition of without a contrast and the second rotary imaging is in the condition of with a contrast. The rotations are performed in the same axial plane. It is possible to extract a two-dimensional image data without a contrast from the plurality of two-dimensional image data acquired by the first rotary imaging and to extract a two-dimensional image data with a contrast, for example, deviated by 0.5° angle from the plurality of two-dimensional image data acquired by the second rotary imaging.

The first rotary imaging and the second rotary imaging can be performed with the use of a floor-suspended arm and a ceiling-suspended arm in a biplane imaging device. For example, the first rotary imaging is performed by rotating the floor-suspended arm, and the second rotary imaging is performed by rotating the ceiling-suspended arm. For the X-ray imaging device shown in FIG. 1, the first rotary imaging is performed by rotating the second X-ray generation unit 21 and the second X-ray detection unit 22 due to the rotation of the C arm 20. The second rotary imaging is performed by rotating the first X-ray generation unit 16 and the first X-ray detection unit 17 due to the rotation of an Ω arm 15.

The rotation of the C arm 20 for the first rotary imaging and the second rotary imaging may be performed by successively twice rotating in either an arrowed W direction or an arrowed Wa direction, as shown in FIG. 8.

Figure 10:
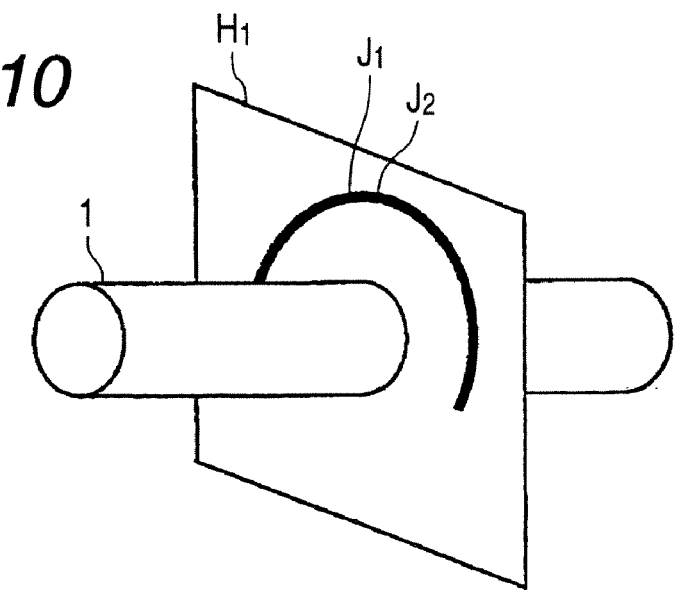
FIG. 10 is a diagram schematically showing that the X-ray generation unit and the X-ray detection unit in the device rotate in the same plane.
Figure 11:
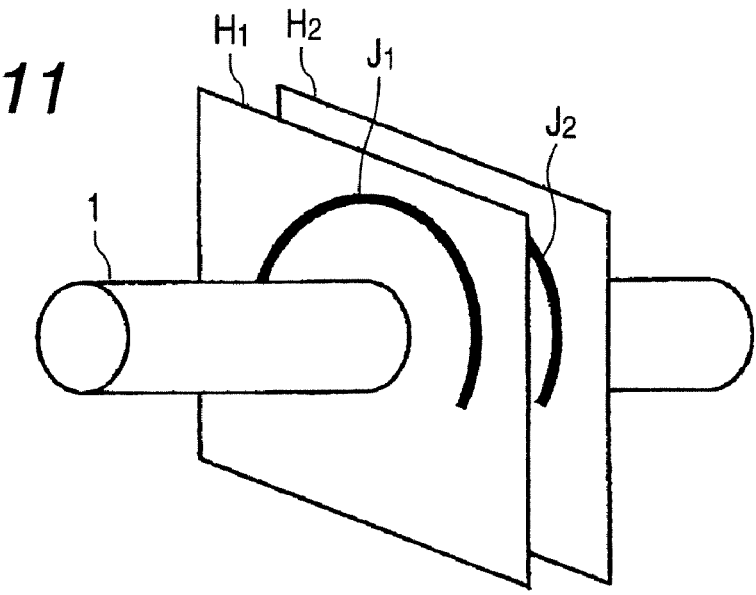
FIG. 11 is a diagram schematically showing that the X-ray generation unit and the X-ray detection unit in the device rotate in the different plane.

As shown in FIG. 10, a first rotation $J_1$ of the X-ray generation unit 21 and the X-ray detection unit 22 in the first rotary imaging and a second rotation $J_2$ of the X-ray generation unit 21 and the X-ray detection unit 22 in the second rotary imaging are performed in a same plane $H_1$. Without being limited by this, as shown in FIG. 11, while the first rotation $J_1$ is performed in the plane $H_1$, the second rotation $J_2$ may be performed in the plane $H_2$ different from the plane $H_1$. For the plane $H_1$ and plane $H_2$, the distance between the plane $H_1$ and the plane $H_2$ is known, and they are distanced only by the range capable of aligning two-dimensional image data acquired by the first rotation $J_1$ with two-dimensional image data acquired by the second rotation $J_2$.

For displaying the blood vessel image data 5, the soft tissue image data 3, and the soft tissue/blood vessel image data 34, of the sample 1 on the monitor 23, any one of the images may be displayed or all of the images may be displayed at the same time. The monitor 23 may display a desired image selected by the operator among the blood vessel image data 5, the soft tissue image data 3, and the soft tissue/blood vessel image data 34. The monitor 23 may switch the display of the blood vessel image data 5, the soft tissue image data 3, and the soft tissue/blood vessel image data 34 at every predetermined period.

Next, the third embodiment of the invention will be described with reference to the accompanying drawings. Since the device shown in FIG. 1 and FIG. 2 has a same configuration, a description thereof will be omitted.

Figure 12:
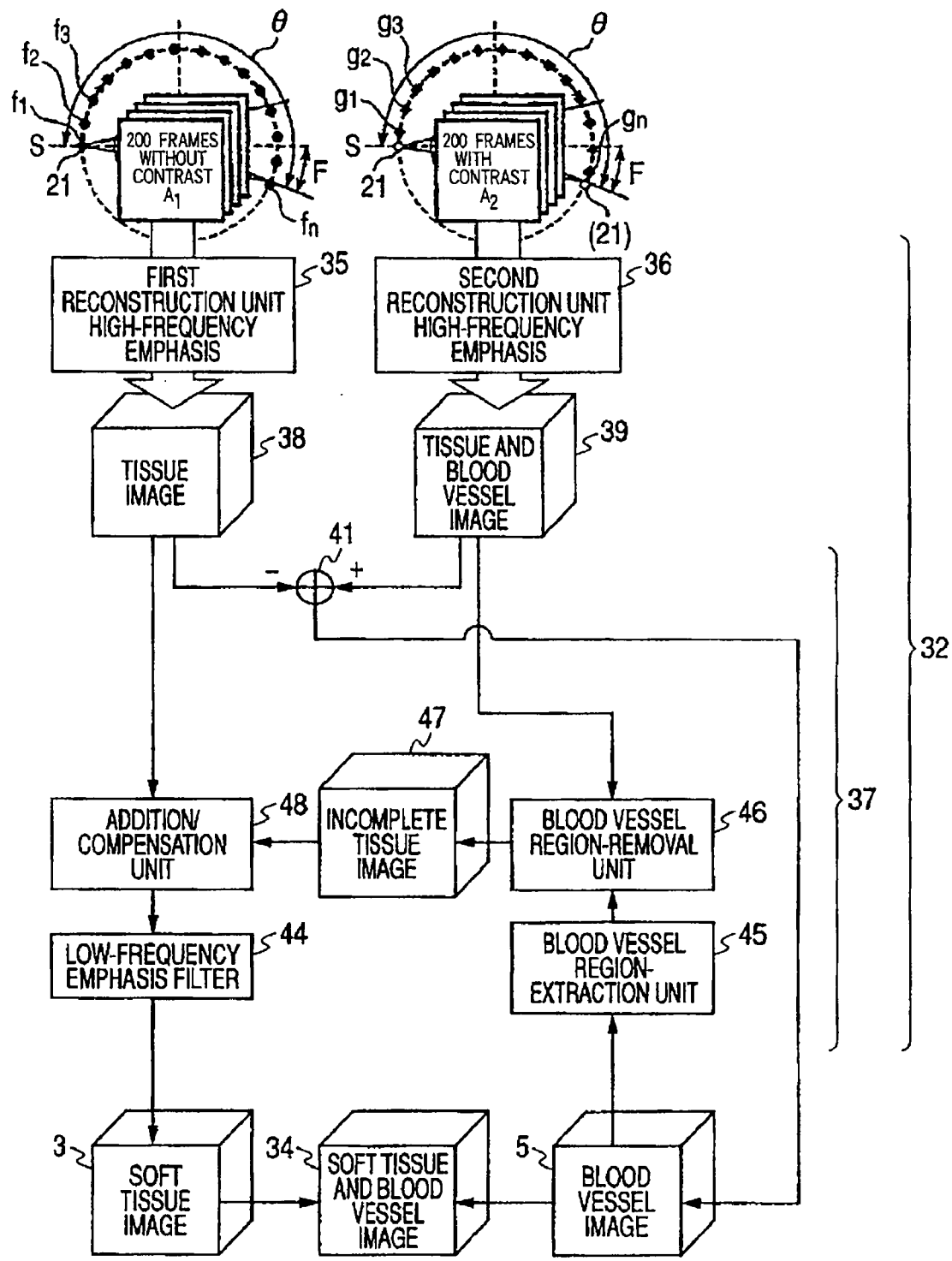
FIG. 12 is a functional block diagram illustrating a reconstruction in a third embodiment of an X-ray imaging device according to the invention.

FIG. 12 is a functional block diagram illustrating an image acquisition of an X-ray imaging device. The first reconstruction unit 35 reads out the plurality of two-dimensional image data $A_1$ acquired by giving no contrast to the sample 1, from the image storage unit 33. The first reconstruction unit 35 allows the reconstruction with the use of two-dimensional image data $A_1$ by applying the reconstruction theory such as Feldkamp method, or the like, and acquires the three-dimensional tissue image data 38 of the sample 1. The first reconstruction unit 35 employs, as for the reconstruction filter, a filter such as Shepp & Logan and Ramachandran, which emphasizes a relatively high-frequency component.

The second reconstruction unit 36 allows the reconstruction with the use of the plurality of two-dimensional image data $A_2$ acquired by giving a contrast to the sample 1, by applying the reconstruction theory such as Feldkamp method, or the like, and acquires the three-dimensional tissue/blood vessel image data 39 including tissues and blood vessels of the sample 1. The second reconstruction unit 36 as in the first reconstruction unit 35 employs, as for the reconstruction filter, a filter such as Shepp & Logan and Ramachandran, which emphasizes a relatively high-frequency component.

The subtracter (first calculation unit) 41 of the inter-image calculation unit 37 calculates the difference between the tissue/blood vessel image data 39 and the tissue image data 38 to acquire the three-dimensional blood vessel image data 5.

The blood vessel region-extraction unit (second calculation unit) 45 extracts the blood vessel region from the three-dimensional blood vessel image data 5 acquired with the subtracter 41. The blood vessel region-extraction unit 45 extracts the blood vessel region from the three-dimensional blood vessel mage data 5, for example, by binarization. The blood vessel image data 5 has a level difference between blood vessels and other tissues. Thus, for the blood vessel image data 5, only the blood vessels can be extracted on the basis of a preliminarily set threshold value.

The blood vessel region-removal unit (second calculation unit) 46 removes the blood vessel region extracted by the blood vessel region-extraction unit 45 from the tissue/blood vessel image data 39 to acquire an incomplete tissue image data 47. The incomplete tissue image data 47 has information on the tissue region, but has no information on the blood vessel region.

The addition/compensation unit (third calculation unit) 48 acquires information on the blood vessel region missed in the incomplete tissue image data 47 from the tissue image data 38, and compensates the acquired information on the blood vessel region to the incomplete tissue image data 47, to obtain a complete tissue image. The addition/compensation unit 48 adds the complete tissue image data 47 obtained by compensation and the tissue image data 38, and acquires the soft tissue image data 3.

Hereinbelow, the reconstruction operation with the device constructed in the above manner will be explained.

As in the above embodiment, the imaging is performed at imaging angle positions $f_1, f_2, \ldots, f_n$. Accordingly, 200 frames of the two-dimensional image data $A_1$ without a contrast are acquired. The imaging is also performed at imaging angle positions $g_1, g_2, \ldots, g_n$. Accordingly, 200 frames of the two-dimensional image data $A_2$ with a contrast are acquired.

The first reconstruction unit 35 reads out the plurality of two-dimensional image data $A_1$ acquired by giving no contrast to the sample 1, from the image storage unit 33. The first reconstruction unit 35 allows the reconstruction with the use of two-dimensional image data $A_1$ by applying the reconstruction theory such as Feldkamp method, or the like, and acquires the three-dimensional tissue image data 38 of the sample 1.

The second reconstruction unit 36 allows the reconstruction with the use of the plurality of two-dimensional image data $A_2$ acquired by giving a contrast to the sample 1, by applying the reconstruction theory such as Feldkamp method, or the like, and acquires the three-dimensional tissue/blood vessel image data 39 including tissues and blood vessels of the sample 1.

The subtracter 41 of the inter-image calculation unit 37 calculates the difference between the tissue/blood vessel image data 39 and the tissue image data 38 to acquire the three-dimensional blood vessel image data 5. Next, the blood vessel region-extraction unit 45 extracts the blood vessel region from the three-dimensional blood vessel image data 5 acquired with the subtracter 41, for example, by binarization. The blood vessel region-removal unit 46 removes the blood vessel region extracted by the blood vessel region-extraction unit 45 from the tissue/blood vessel image data 39 to acquire the incomplete tissue image data 47. Then, the addition/compensation unit 48 acquires information on the blood vessel region missed in the incomplete tissue image data 47 from the tissue image data 38. The addition/compensation unit 48 compensates the acquired information on the blood vessel region to the incomplete tissue image data 47, to obtain a complete tissue image. The addition/compensation unit 48 adds the complete tissue image data 47 obtained by compensation and the tissue image data 38, and acquires the soft tissue image data 3.

The low-frequency emphasis filter 44 emphasizes a low-frequency component with the use of a relatively strong low-frequency emphasis filter for the body axis direction, and emphasizes a low-frequency component with the use of a relatively weak low-frequency emphasis filter for the Axial direction, in the soft tissue image data 3.

The inter-image calculation unit 37 adds the blood vessel image data 5 and the soft tissue image data 3 to acquire the three-dimensional soft tissue/blood vessel image data 34. These blood vessel image data 5, the soft tissue image data 3, and the soft tissue/blood vessel image data 34, of the sample 1, are displayed on the monitor 23.

According to the above-mentioned third embodiment, there is no doubt about achieving the same effect as in the first embodiment. According to the third embodiment, since the blood vessel region-extraction unit 45 extracts the blood vessel region from the three-dimensional blood image data 5, for example, by binarization and the blood vessel region-removal unit 46 removes the extracted blood vessel region from the tissue/blood vessel image data 39, the artifact effect in the blood vessel image data 5 can be reduced.

Next, the fourth embodiment of the invention will be described with reference to the accompanying drawings. Since the device shown in FIG. 1 and FIG. 2 has a same configuration, a description thereof will be omitted.

Figure 13:
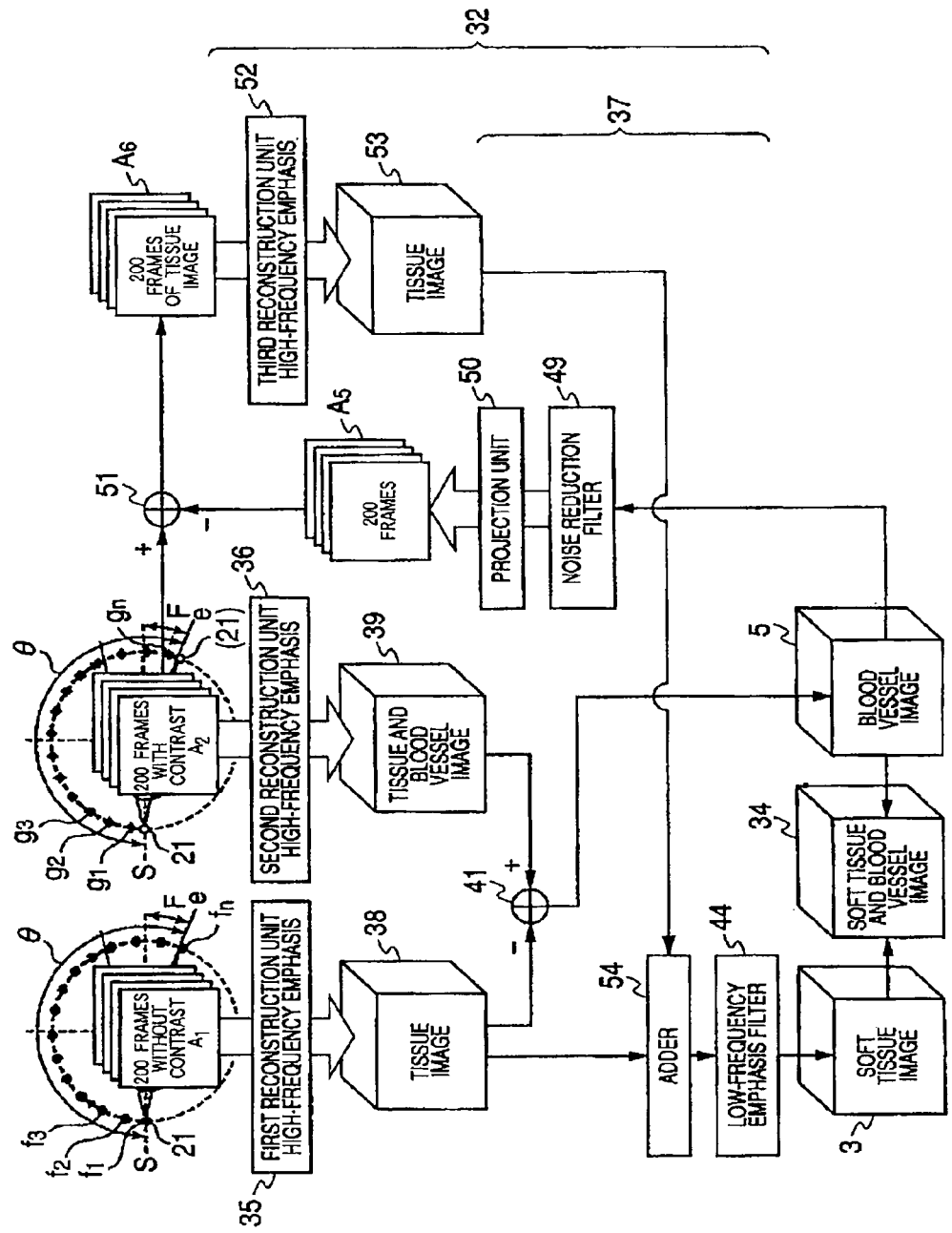
FIG. 13 is a functional block diagram illustrating a reconstruction in a fourth embodiment of an X-ray imaging device according to the invention.

FIG. 13 is a functional block diagram illustrating an image acquisition of an X-ray imaging device. A noise reduction filter 49 reduces the noise in the three-dimensional blood vessel image data 5. The noise reduction filter 49, for example, employs a median filter. The noise reduction filter 49 is not limited by the median filter, and various noise reduction filters can also be employed.

A projection unit 50 projects the three-dimensional blood vessel image data 5 to give a plurality of two-dimensional image data of blood vessels, i.e., 200 frames of the two-dimensional image data $A_5$. The two-dimensional image data $A_5$ of blood vessels is acquired by projecting at angles corresponding to imaging angle positions $g_1, g_2, \ldots, g_n$ for 200 frames of two-dimensional image data $A_2$ which are imaged under a condition of with a contrast. That is, the two-dimensional image data $A_5$ of blood vessels is acquired by projecting at imaging angle positions $g_1, g_2, \ldots, g_n$, which are stepped by $\phi$ angle (=1°), during the rotation performed within the imaging range of $\theta$ and start rotating from the rotation start angle position sa, which is the position deviated by $\phi/2$ angle e.g., 0.5° angle with respect to the rotation start angle position S, to the rotation end angle position en.

The subtracter (second calculation unit) 51 subtracts 200 frames of the two-dimensional image data $A_5$ of blood vessels from the 200 frames of two-dimensional image data $A_2$ which are imaged under a condition of with a contrast, and acquires 200 frames of a tissue image data $A_6$.

The third reconstruction unit 52 allows the reconstruction with the use of 200 frames of the tissue image data $A_6$ by applying the reconstruction theory such as Feldkamp method, or the like, and acquires a three-dimensional tissue image data 53 including tissues of the sample 1. The third reconstruction unit 52 as in the first reconstruction unit 35 employs, as for the reconstruction filter, a filter such as Shepp & Logan and Ramachandran, which emphasizes a relatively high-frequency component.

The adder (third calculation unit) 54 adds the three-dimensional tissue image data 53 acquired by the third reconstruction unit 52 and the three-dimensional tissue image data 38 acquired by the first reconstruction unit 35, to acquire the three-dimensional soft tissue image data 3.

Hereinbelow, the reconstruction operation with the device constructed in the above manner will be explained.

As in the above embodiment, the imaging is performed at imaging angle positions $f_1, f_2, \ldots, f_n$. Accordingly, 200 frames of the two-dimensional image data $A_1$ without a contrast are acquired. The imaging is also performed at imaging angle positions $g_1, g_2, \ldots, g_n$. Accordingly, 200 frames of the two-dimensional image data $A_2$ with a contrast are acquired.

The first reconstruction unit 35 reads out the plurality of two-dimensional image data $A_1$ acquired by giving no contrast to the sample 1, from the image storage unit 33. The first reconstruction unit 35 allows the reconstruction with the use of two-dimensional image data $A_1$ by applying the reconstruction theory such as Feldkamp method, or the like, and acquires the three-dimensional tissue image data 38 of the sample 1.

The second reconstruction unit 36 allows the reconstruction with the use of the plurality of two-dimensional image data $A_2$ acquired by giving a contrast to the sample 1, by applying the reconstruction theory such as Feldkamp method, or the like, and acquires the three-dimensional tissue/blood vessel image data 39 including tissues and blood vessels of the sample 1.

The subtracter 41 of the inter-image calculation unit 37 calculates the difference between the tissue/blood vessel image data 39 and the tissue image data 38 to acquire the three-dimensional blood vessel image data 5. Next, the noise reduction filter 49 reduces the noise in the three-dimensional blood vessel image data 5, and then sends to the projection unit 50.

The projection unit 50 inputs the noise reduced three-dimensional blood vessel image data 5, and projects the three-dimensional blood vessel image data 5 to give a plurality of two-dimensional image data of blood vessels, i.e., 200 frames of the two-dimensional image data $A_5$. The two-dimensional image data $A_5$ of blood vessels is acquired in the same manner as above such as by projecting at angles corresponding to imaging angle positions $g_1, g_2, \ldots, g_n$ for 200 frames of two-dimensional image data $A_2$ which are imaged under a condition of with a contrast.

The subtracter 51 subtracts 200 frames of the two-dimensional image data $A_5$ of blood vessels from the 200 frames of two-dimensional image data $A_2$ which are imaged under a condition of with a contrast, and acquires 200 frames of the tissue image data $A_6$.

The third reconstruction unit 52 allows the reconstruction with the use of 200 frames of the tissue image data $A_6$ by applying the reconstruction theory such as Feldkamp method, or the like, and acquires the three-dimensional tissue image data 53 including tissues of the sample 1.

The adder 54 adds the three-dimensional tissue image data 53 acquired by the third reconstruction unit 52 and the three-dimensional tissue image data 38 acquired by the first reconstruction unit 35, to acquire the three-dimensional soft tissue image data 3.

The low-frequency emphasis filter 44 emphasizes a low-frequency component with the use of a relatively strong low-frequency emphasis filter for the body axis direction, and emphasizes a low-frequency component with the use of a relatively weak low-frequency emphasis filter for the Axial direction, in the three-dimensional soft tissue image data 3.

Next, the inter-image calculation unit 37 adds the blood vessel image data 5 and the soft tissue image data 3 to acquire the three-dimensional soft tissue/blood vessel image data 34. These blood vessel image data 5, the soft tissue image data 3, and the soft tissue/blood vessel image data 34, of the sample 1, are displayed on the monitor 23.

According to the above-mentioned fourth embodiment, there is no doubt about achieving the same effect as in the first embodiment. According to the fourth embodiment, a plurality of the two-dimensional image data $A_5$ of blood vessels is acquired by projecting the three-dimensional blood vessel image data 5, the tissue image data $A_6$ is acquired from the difference between the two-dimensional image data $A_5$ of blood vessels and two-dimensional image data $A_2$ imaged under a contrast, and then the three-dimensional tissue image data 53 is acquired by performing the reconstruction with the use of the tissue image data $A_6$. In this manner, the artifact effect in the blood vessel image data 5 can be reduced as the addition from many directions is achieved at the time of the reconstruction.

Next, the fifth embodiment of the invention will be described with reference to the accompanying drawings.

Since the device shown in FIG. 1 and FIG. 2 has a same configuration, a description thereof will be omitted.

Figure 14:
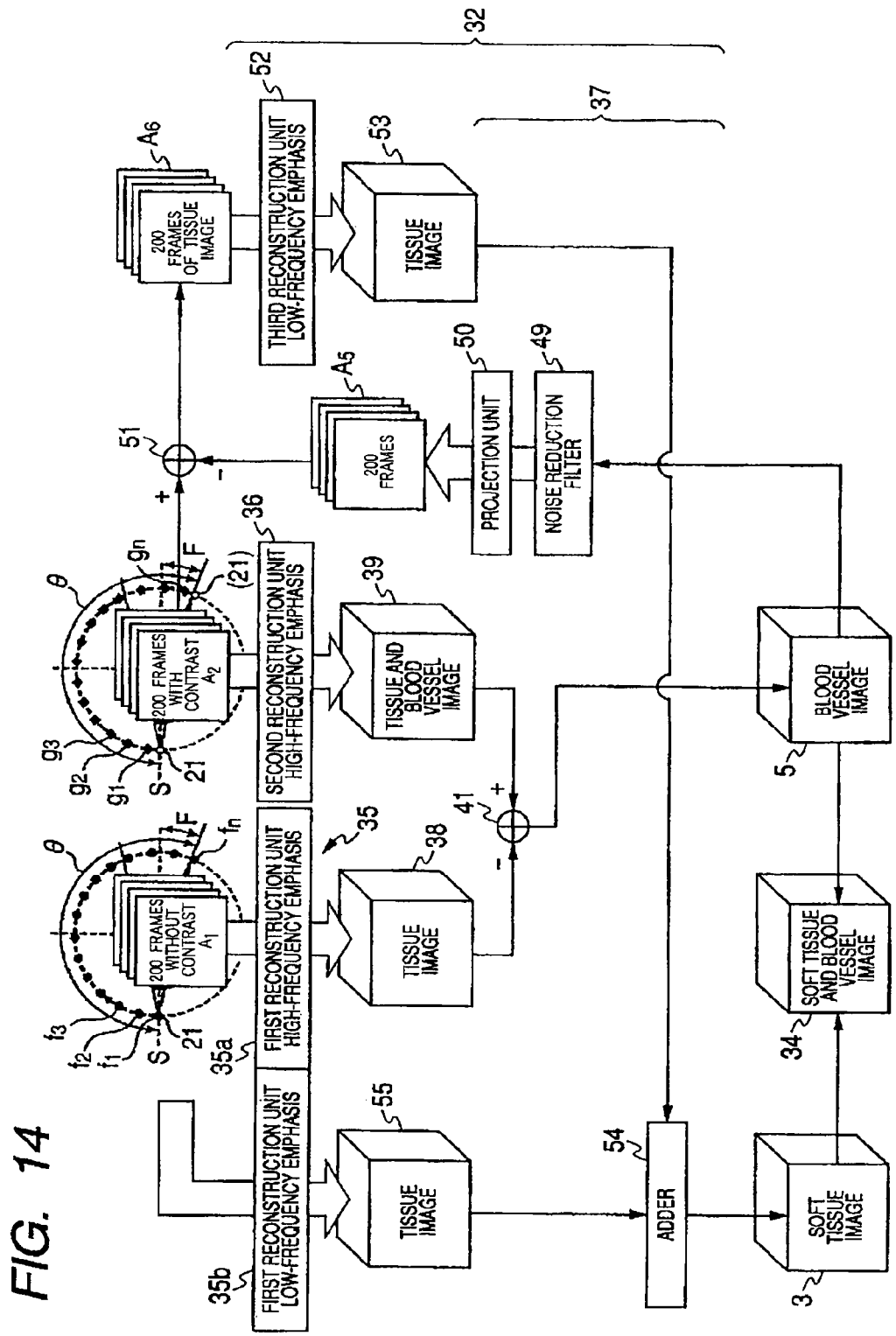
FIG. 14 is a functional block diagram illustrating a reconstruction in a fifth embodiment of an X-ray imaging device according to the invention.

FIG. 14 is a functional block diagram illustrating an image acquisition of an X-ray imaging device. The first reconstruction unit 35 is provided with a first reconstruction unit 35a and a first reconstruction unit 35b. The first reconstruction unit 35a reads out the plurality of two-dimensional image data $A_1$ acquired by giving no contrast to the sample 1, from the image storage unit 33. The first reconstruction unit 35a allows the reconstruction with the use of two-dimensional image data $A_1$ by applying the reconstruction theory such as Feldkamp method, or the like, and acquires the three-dimensional tissue image data 38 of the sample 1.

The first reconstruction unit 35b employs, as for the reconstruction filter, a filter such as Shepp & Logan and Ramachandran, which emphasizes a relatively high-frequency component, and a low-frequency emphasis filter which emphasizes a low-frequency component.

The third reconstruction unit 52 allows the reconstruction with the use of 200 frames of the tissue image data $A_6$ by applying the reconstruction theory such as Feldkamp method, or the like, and acquires the three-dimensional tissue image data 53 including tissues of the sample 1. The third reconstruction unit 52 as in the first reconstruction unit 35 employs, as for the reconstruction filter, a low-frequency component filter emphasizing a low-frequency component.

In the present embodiment, the low-frequency emphasis filter 44 for the fourth embodiment is excluded.

Hereinbelow, the reconstruction operation with the device constructed in the above manner will be explained.

As in the above embodiment, the imaging is performed at imaging angle positions $f_1, f_2, \ldots, f_n$. Accordingly, 200 frames of the two-dimensional image data $A_1$ without a contrast are acquired. The imaging is also performed at imaging angle positions $g_1, g_2, \ldots, g_n$. Accordingly, 200 frames of the two-dimensional image data $A_2$ with a contrast are acquired.

The first reconstruction unit 35a reads out the plurality of two-dimensional image data $A_1$ acquired by giving no contrast to the sample 1, from the image storage unit 33. The first reconstruction unit 35a allows the reconstruction with the use of two-dimensional image data $A_1$ and a filter emphasizing a high-frequency component, and the three-dimensional tissue image data 38 of the sample 1 is acquired.

In addition, the first reconstruction unit 35b reads out the plurality of two-dimensional image data $A_1$ acquired by giving no contrast to the sample 1, from the image storage unit 33. The first reconstruction unit 35b allows the reconstruction with the use of two-dimensional image data $A_1$ and a filter emphasizing a low-frequency component, and the three-dimensional tissue image data 55 of the sample 1 is acquired.

The second reconstruction unit 36 allows the reconstruction with the use of the plurality of two-dimensional image data $A_2$ acquired by giving a contrast to the sample 1, and acquires the three-dimensional tissue/blood vessel image data 39 including tissues and blood vessels of the sample 1.

The subtracter 41 of the inter-image calculation unit 37 calculates the difference between the tissue/blood vessel image data 39 and the tissue image data 38 to acquire the three-dimensional blood vessel image data 5. Next, the noise reduction filter 49 reduces the noise in the three-dimensional blood vessel image data 5, and then sends to the projection unit 50. The projection unit 50 projects the three-dimensional blood vessel image data 5 to give a plurality of two-dimensional image data of blood vessels, i.e., 200 frames of the two-dimensional image data $A_5$. The subtracter 51 subtracts 200 frames of the two-dimensional image data $A_5$ of blood vessels from the 200 frames of two-dimensional image data $A_2$ which are imaged under a condition of with a contrast, and acquires 200 frames of the tissue image data $A_6$.

The third reconstruction unit 52 allows the reconstruction with the use of 200 frames of the tissue image data $A_6$ by applying the reconstruction theory such as Feldkamp method, or the like, and acquires the three-dimensional tissue image data 53 including tissues of the sample 1.

The adder 54 adds the three-dimensional tissue image data 53 acquired by the third reconstruction unit 52 and the three-dimensional tissue image data 55 reconstructed by the first reconstruction unit 35, to acquire the three-dimensional soft tissue image data 3.

The inter-image calculation unit 37 adds the blood vessel image data 5 and the soft tissue image data 3 to acquire the three-dimensional soft tissue/blood vessel image data 34. These blood vessel image data 5, the soft tissue image data 3, and the soft tissue/blood vessel image data 34, of the sample 1, are displayed on the monitor 23.

According to the above-mentioned fifth embodiment, there is no doubt about achieving the same effect as in the first embodiment. According to the fifth embodiment, the first reconstruction unit 35 allows the reconstruction with the use of the two-dimensional image data $A_1$ and a filter emphasizing a low-frequency component to acquire the three-dimensional tissue image data 55 of the sample 1. Accordingly, there is no need for the low-frequency emphasis filter 44 to be provided for after the reconstruction.

Next, the sixth embodiment of the invention will be described with reference to the accompanying drawings. Since the device shown in FIG. 1 and FIG. 2 has a same configuration, a description thereof will be omitted.

Figure 15:
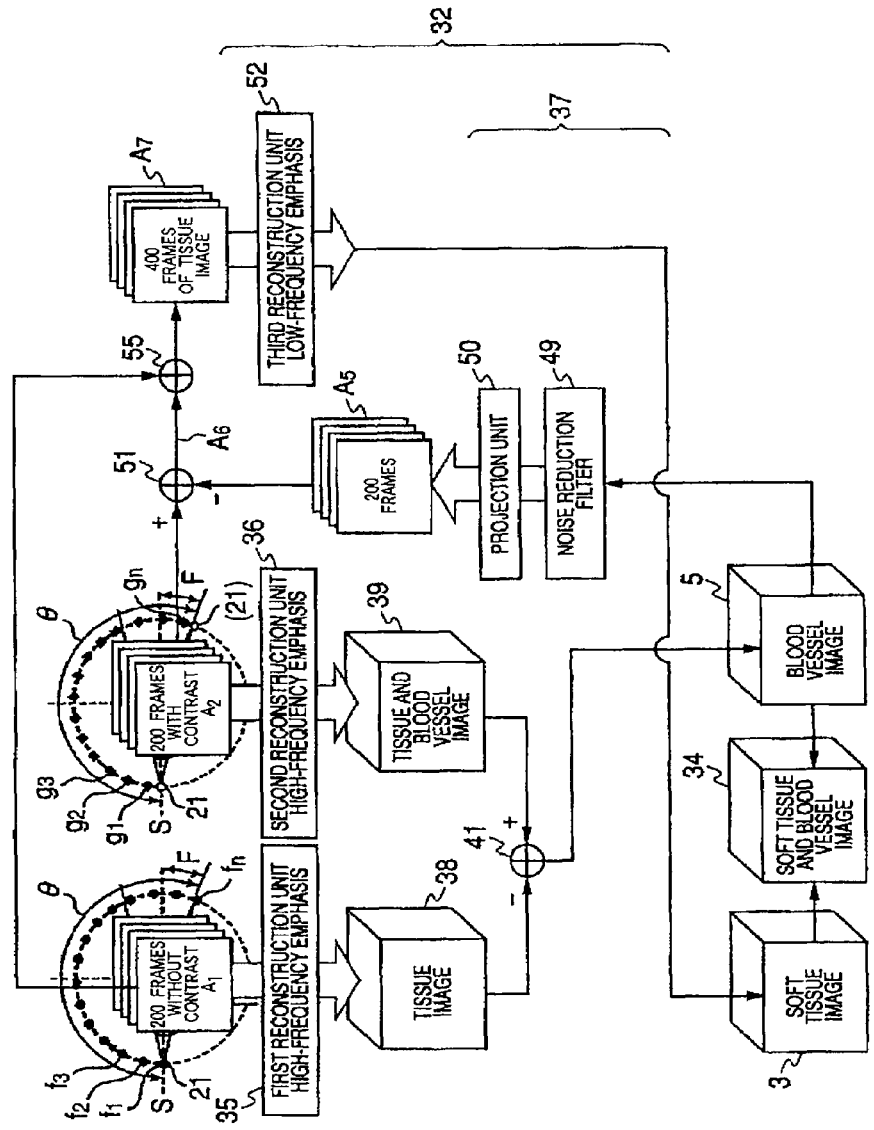
FIG. 15 is a functional block diagram illustrating a reconstruction in a sixth embodiment of an X-ray imaging device according to the invention.

FIG. 15 is a functional block diagram illustrating an image acquisition of an X-ray imaging device. An integrator 55 is connected on the output side of the subtracter 51. The integrator 55t inputs 200 frames of the tissue image data $A_6$ outputted from the subtracter 51, which is the difference between 200 frames of two-dimensional image data $A_2$ imaged with a contrast and 200 frames of the two-dimensional image $A_5$ of blood vessels. The integrator 55t combines the tissue image data $A_6$ and the two-dimensional image data $A_1$ to acquire 400 frames of a two-dimensional tissue image data $A_7$.

The third reconstruction unit 52 allows the reconstruction with the use of 400 frames of the tissue image data $A_7$ by applying the reconstruction theory such as Feldkamp method, or the like, and acquires the three-dimensional tissue image data 3 including tissues of the sample 1. The third reconstruction unit 52 employs, as for the reconstruction filter, a low-frequency filter which emphasizes a low-frequency component.

Hereinbelow, the reconstruction operation with the device constructed in the above manner will be explained.

As in the above embodiment, the imaging is performed at imaging angle positions $f_1, f_2, \ldots, f_n$. Accordingly, 200 frames of the two-dimensional image data $A_1$ without a contrast are acquired. The imaging is also performed at imaging angle positions $g_1, g_2, \ldots, g_n$. Accordingly, 200 frames of the two-dimensional image data $A_2$ with a contrast are acquired.

The first reconstruction unit 35 reads out the plurality of two-dimensional image data $A_1$ acquired by giving no contrast to the sample 1, from the image storage unit 33. The first reconstruction unit 35 allows the reconstruction with the use of two-dimensional image data $A_1$ and a filter emphasizing a high-frequency component, and acquires the three-dimensional tissue image data 38 of the sample 1.

The second reconstruction unit 36 allows the reconstruction with the use of the plurality of two-dimensional image data $A_2$ acquired by giving a contrast to the sample 1 and a filter emphasizing a high-frequency component, and acquires the three-dimensional tissue/blood vessel image data 39 including tissues and blood vessels of the sample 1.

The subtracter 41 calculates the difference between the tissue/blood vessel image data 39 and the tissue image data 38 to acquire the three-dimensional blood vessel image data 5. Next, the noise reduction filter 49 reduces the noise in the three-dimensional blood vessel image data 5, and then sends to the projection unit 50. The projection unit 50 projects the three-dimensional blood vessel image data 5 to give a plurality of two-dimensional image data of blood vessels, i.e., 200 frames of the two-dimensional image data $A_5$. The subtracter 51 subtracts 200 frames of the two-dimensional image data $A_5$ of blood vessels from the 200 frames of two-dimensional image data $A_2$ which are imaged under a condition of with a contrast, and acquires 200 frames of the tissue image data $A_6$.

The integrator 55 inputs 200 frames of the tissue image data $A_6$ outputted from the subtracter 51, which is the difference between 200 frames of two-dimensional image data $A_2$ imaged with a contrast and 200 frames of the two-dimensional image $A_5$ of blood vessels. The integrator 55 combines the tissue image data $A_6$ and the two-dimensional image data $A_1$ to acquire 400 frames of the two-dimensional tissue image data $A_7$.

The third reconstruction unit 52 allows the reconstruction with the use of 400 frames of the two-dimensional tissue image data $A_7$ and a low-frequency filter emphasizing a low-frequency component, and acquires the three-dimensional image data 3 including tissues of the sample 1.

The inter-image calculation unit 37 adds the blood vessel image data 5 and the soft tissue image data 3 to acquire the three-dimensional soft tissue/blood vessel image data 34. These blood vessel image data 5, the soft tissue image data 3, and the soft tissue/blood vessel image data 34, of the sample 1, are displayed on the monitor 23.

According to the above-mentioned sixth embodiment, there is no doubt about achieving the same effect as in the first embodiment. According to the sixth embodiment, before performing the reconstruction, 200 frames of the tissue image data $A_6$, which is the difference between two-dimensional image data $A_2$ imaged with a contrast and the two-dimensional image $A_5$ of blood vessels, are inputted, and the two-dimensional tissue image data $A_7$ is acquired by combining the tissue image data $A_6$ and the two-dimensional image data $A_1$. The reconstruction is performed with the use of the two-dimensional tissue image data $A_7$ and a low-frequency filter emphasizing a low-frequency component to acquire the three-dimensional tissue image data 3. In this manner, the same effect as in the first embodiment is achieved without a doubt, and the low-frequency emphasis filter 44 is not necessarily provided for after the reconstruction.

Next, the seventh embodiment of the invention will be described with reference to the accompanying drawings. Since the device shown in FIG. 1 and FIG. 2 has a same configuration, a description thereof will be omitted.

Figure 16:
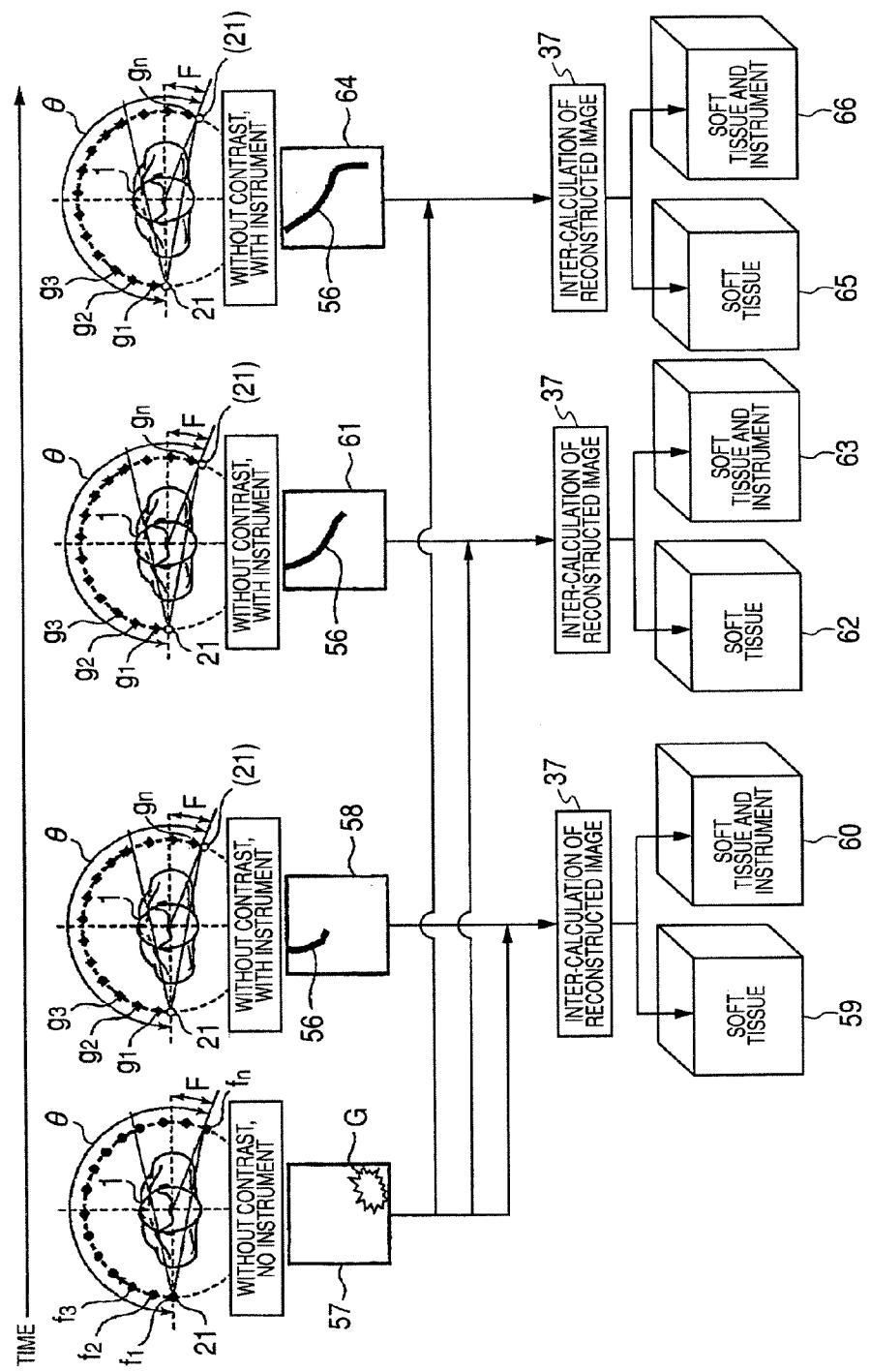
FIG. 16 is a flow diagram illustrating an application of image acquisition in a seventh embodiment of an X-ray imaging device according to the invention.
Figure 17:
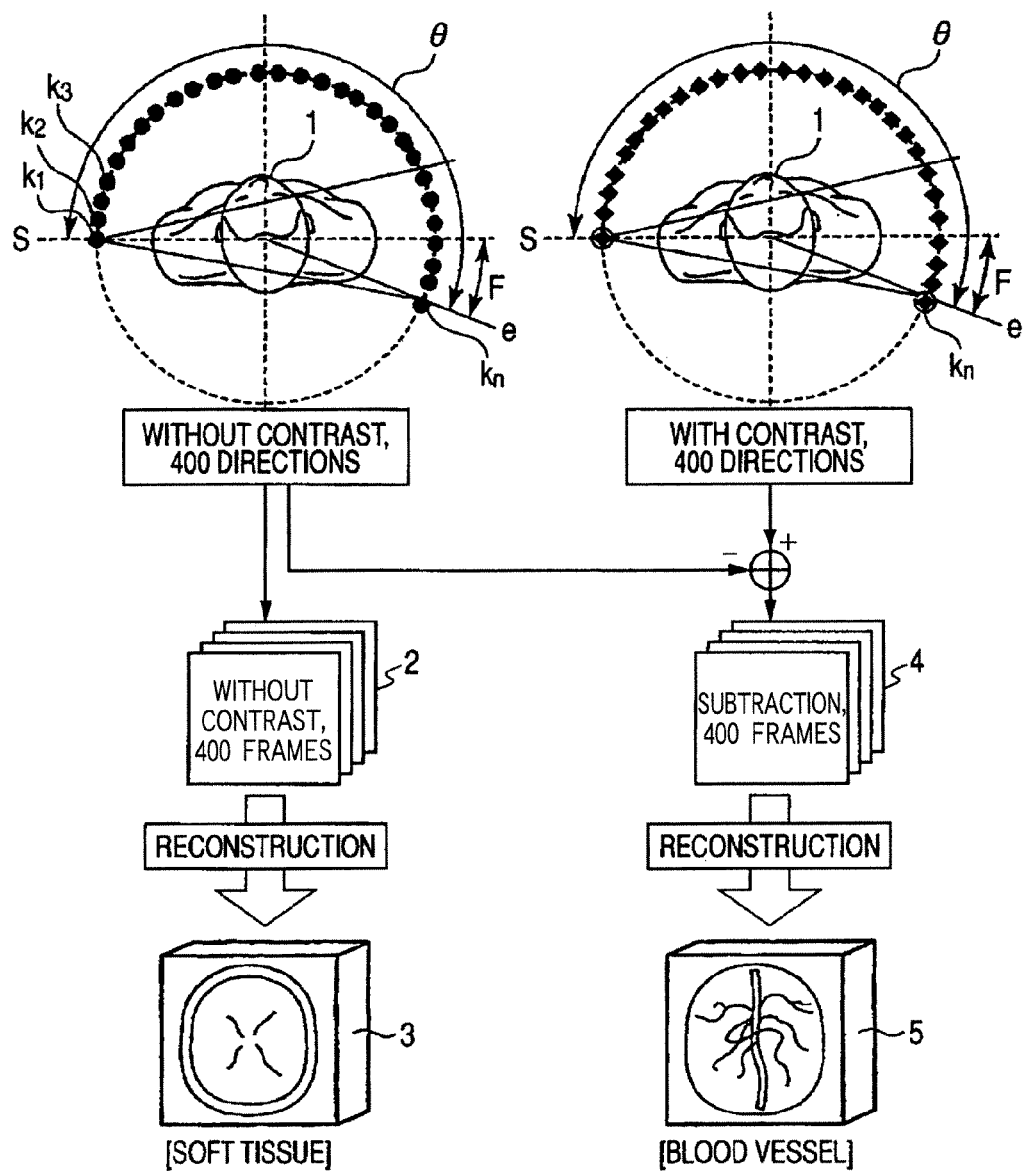
FIG. 17 is a diagram illustrating the passage of acquiring images of soft tissues and blood vessels in accordance with a known X-ray imaging method.

FIG. 16 is a flow diagram illustrating an application of an image acquisition for a navigation surgery. For an X-ray imaging device, any of X-ray imaging devices described in the first to sixth embodiment can be employed. Herein, a display example of a surgical instrument 56 for approaching a soft tissue lesion G such as cancer in the sample 1 will be described.

In a state that the surgical instrument 56 is not inserted into the sample 1 and a contrast agent is not injected into the sample 1, the imaging at imaging angle positions (first angle) $f_1, f_2, \ldots, f_n$ is performed as in the above manner. Accordingly, 200 frames of the two-dimensional image data without a contrast are acquired. The first reconstruction unit 35 allows the reconstruction with the use of the plurality of two-dimensional image data acquired by giving no contrast to the sample 1, and acquires a three-dimensional tissue image data (first reconstruction image) 57 of the sample 1. The tissue image data 57 shows the soft tissue lesion G. The tissue image data 57 is, for example, stored in the image storage unit 33.

Next, in a state that the surgical instrument 56 is inserted into the sample 1 and still the contrast agent is not injected into the sample 1, the imaging at imaging angle positions (second angle which is deviated from the first angle) $g_1$, $g_2, \ldots, g_n$ is performed. Accordingly, 200 frames of a two-dimensional image data without a contrast are acquired. The second reconstruction unit 36 allows the reconstruction with the use of 200 frames of two-dimensional image data acquired by giving no contrast to the sample 1, and acquires a three-dimensional soft tissue/instrument image data (second reconstruction image) 58 of the sample 1. On the soft tissue/instrument image data 58, the surgical instrument 56 for approaching the soft tissue lesion G is imaged.

The inter-image calculation unit 37 carries out an inter-calculation between the tissue image data 57 reconstructed by the first reconstruction unit 35 and the soft tissue/instrument image data 58 reconstructed by the second reconstruction unit 36, and thus acquires a three-dimensional soft tissue image data 59 and a three-dimensional soft tissue/instrument image data 60.

The approach of the surgical instrument 56 in the sample 1 is further processed, and the contrast agent is not injected into the sample 1. In this state, the imaging at imaging angle positions $g_1, g_2, \ldots, g_n$ is again performed. Accordingly, 200 frames of a two-dimensional image data without a contrast are acquired. The second reconstruction unit 36 allows the reconstruction with the use of 200 frames of the two-dimensional image data acquired by giving no contrast to the sample 1, and acquires a three-dimensional soft tissue/instrument image data (second reconstruction image) 61 of the sample 1. On the soft tissue/instrument image data 61, the surgical instrument 56 which is further inserted to the sample 1 is imaged.

The inter-calculation unit 37 reads out the tissue image data 57 stored in the image storage unit 33. The inter-image calculation unit 37 carries out an inter-calculation between the tissue image data 57 and the soft tissue/instrument image data 61 reconstructed by the second reconstruction unit 36, and thus acquires a three-dimensional soft tissue image data 62 and a three-dimensional soft tissue/instrument image data 63.

The approach of the surgical instrument 56 in the sample 1 is further processed, and the contrast agent is not injected into the sample 1. In this state, the imaging at imaging angle positions $g_1, g_2, \ldots, g_n$ is again performed. Accordingly, 200 frames of a two-dimensional image data without a contrast are acquired. The second reconstruction unit 36 allows the reconstruction with the use of 200 frames of the two-dimensional image data acquired by giving no contrast to the sample 1, and acquires a three-dimensional soft tissue/instrument image data (second reconstruction image) 64 of the sample 1. On the soft tissue/instrument image data 64, the surgical instrument 56 which is further inserted to the sample 1 is imaged.

The inter-image calculation unit 37 again reads out the tissue image data 57 stored in the image storage unit 33. The inter-image calculation unit 37 carries out an inter-calculation between the tissue image data 57 and the soft tissue/instrument image data 64 reconstructed by the second reconstruction unit 36, and thus acquires a three-dimensional soft tissue image data 65 and a three-dimensional soft tissue/instrument image data 66.

The approach of the surgical instrument 56 into the sample 1 and the imaging at imaging angle positions $g_1, g_2, \ldots, g_n$ are repeatedly carried out. Accordingly, the three-dimensional soft tissue image data 59, 62, and 65, and the three-dimensional soft tissue/instrument image data 60, 63, and 66 imaging the surgical instrument 56 inserted into the sample 1, are acquired.

According to the seventh embodiment, the tissue image data 57 showing the soft tissue lesion G, which is acquired by imaging at imaging angle positions $f_1, f_2, \ldots, f_n$ under conditions of not introducing the surgical instrument 56 and not injecting a contrast agent into the sample 1, is stored in the image storage unit 33. Thereafter, soft tissue/instrument image data 58, 61, and 64 are acquired by several times performing the imaging at imaging angle positions $g_1, g_2, \ldots, g_n$, with a time interval. The reconstruction of each of the soft tissue/instrument image data 58, 61, and 64 with the tissue image data 57 is performed, respectively. Accordingly, three-dimensional soft tissue image data 59, 62, and 65 and three-dimensional soft tissue/instrument image data 60, 63, and 66, are acquired.

As a result, a positional relationship between the surgical instrument 56 for approaching the sample 1 and soft tissues can be confirmed in three dimensions. The tissue image data 57 showing the soft tissue lesion G is acquired by performing the initial imaging at imaging angle positions $f_1, f_2, \ldots, f_n$, and then stored in the image storage unit 33. In this manner, the imaging at imaging angle positions $f_1, f_2, \ldots, f_n$ can be omitted from the second round performance. Therefore, the imaging can be carried out only at imaging angle positions $g_1, g_2, \ldots, g_n$. The time required for acquiring each of three-dimensional soft tissue/instrument image data 60, 63, and 66 can be reduced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray imaging device comprising:
   an X-ray generation unit which emits X-rays to a sample;
   an X-ray detection unit which detects the amount of X-rays passing through the sample;
   an imaging control unit which two or more times rotate the X-ray generation unit and the X-ray detection unit around the sample as a rotation center and imaging the sample at a plurality of rotation angles different from each other during the rotation; and
   an image calculation unit which acquires a three-dimensional image of the sample by performing a calculation process including at least a reconstruction to the plurality of two-dimensional images which are acquired by performing imaging during the rotations of the X-ray generation unit and the X-ray detection unit, the image calculation unit including:
   a first reconstruction unit which acquires a tissue image of the sample by performing a reconstruction to the two-dimensional images acquired from the sample without a contrast,
   a second reconstruction unit which acquires a tissue/blood vessel image including tissues and blood vessels of the sample by performing a reconstruction to the two-dimensional images acquired from the sample with a contrast, and an inter-image calculation unit which acquires a three-dimensional soft tissue image, a three-dimensional soft tissue/blood vessel image, and a three-dimensional blood vessel image, by performing an inter-calculation between the tissue image and the tissue/blood vessel image, the inter-image calculation unit including:

a first calculation unit which acquires the blood vessel image from the difference between the tissue image and the tissue/blood vessel image, a second calculation unit which acquires a tissue image from the difference between the blood vessel image acquired by the first calculation unit and the tissue/blood vessel image acquired by the second reconstruction unit, a third calculation unit which acquires the soft tissue image by adding the tissue image acquired by the second calculation unit and the tissue image acquired by the first reconstruction unit, and a fourth calculation unit which acquires the soft tissue/blood vessel image by adding the blood vessel image acquired by the first calculation unit and the soft tissue image acquired by the third calculation unit.

2. The X-ray imaging device according to claim 1, further comprising a low-frequency component emphasis filter which emphasizes a low-frequency component of the soft tissue image acquired by the third calculation unit.

3. An X-ray imaging device comprising:

an X-ray generation unit which emits X-rays to a sample;

an X-ray detection unit which detects the amount of X-rays passing through the sample;

an imaging control unit which two or more times rotate the X-ray generation unit and the X-ray detection unit around the sample as a rotation center and imaging the sample at a plurality of rotation angles different from each other during the rotation; and an image calculation unit which acquires a three-dimensional image of the sample by performing a calculation process including at least a reconstruction to the plurality of two-dimensional images which are acquired by performing imaging during the rotations of the X-ray generation unit and the X-ray detection unit, the image calculation unit including:

a first reconstruction unit which acquires a tissue image of the sample by performing a reconstruction to the two-dimensional images acquired from the sample without a contrast, a second reconstruction unit which acquires a tissue/blood vessel image including tissues and blood vessels of the sample by performing a reconstruction to the two-dimensional images acquired from the sample with a contrast, and an inter-image calculation unit which acquires a three-dimensional soft tissue image, a three-dimensional soft tissue/blood vessel image, and a three-dimensional blood vessel image, by performing an inter-calculation between the tissue image and the tissue/blood vessel image, the inter-image calculation unit including:

a first calculation unit which acquires the blood vessel image from the difference between the tissue image and the tissue/blood vessel image, a second calculation unit which acquires an incomplete tissue image not including the blood vessel region on the basis of the blood vessel image acquired by the first calculation unit and the tissue/blood vessel image acquired by the second reconstruction unit, a third calculation unit which acquires the soft tissue image by adding the blood vessel region from the tissue image acquired by the first reconstruction unit to the incomplete tissue image acquired by the second calculation unit, and a fourth calculation unit which acquires the soft tissue/blood vessel image by adding the blood vessel image acquired by the first calculation unit and the soft tissue image acquired by the third calculation unit.

4. The X-ray imaging device according to 3, further comprising a low-frequency component emphasis filter which emphasizes a low-frequency component in the soft tissue image acquired by the third calculation unit.

5. An X-ray imaging device comprising:

an X-ray generation unit which emits X-rays to a sample;

an X-ray detection unit which detects the amount of X-rays passing through the sample;

an imaging control unit which two or more times rotate the X-ray generation unit and the X-ray detection unit around the sample as a rotation center and imaging the sample at a plurality of rotation angles different from each other during the rotation; and an image calculation unit which acquires a three-dimensional image of the sample by performing a calculation process including at least a reconstruction to the plurality of two-dimensional images which are acquired by performing imaging during the rotations of the X-ray generation unit and the X-ray detection unit, the image calculation unit including:

a first reconstruction unit which acquires a tissue image of the sample by performing a reconstruction to the two-dimensional images acquired from the sample without a contrast, a second reconstruction unit which acquires a tissue/blood vessel image including tissues and blood vessels of the sample by performing a reconstruction to the two-dimensional images acquired from the sample with a contrast, and an inter-image calculation unit which acquires a three-dimensional soft tissue image, a three-dimensional soft tissue/blood vessel image, and a three-dimensional blood vessel image, by performing an inter-calculation between the tissue image and the tissue/blood vessel image, the inter-image calculation unit including:

a first calculation unit which acquires the blood vessel image from the difference between the tissue image and the tissue/blood vessel image, a projection image unit which acquires a plurality of two-dimensional images by projecting the blood vessel image acquired by the first calculation unit, a second calculation unit which acquires a plurality of tissue images from the difference between the two-dimensional images acquired by the projection image unit and the two-dimensional images acquired from the sample with a contrast, a third reconstruction unit which acquires a tissue image by performing a reconstruction to the tissue images acquired by the second calculation unit, a third calculation unit which acquires the soft tissue image by adding the tissue image acquired by the third reconstruction unit and the tissue image acquired by the first reconstruction unit, and a fourth calculation unit which acquires the soft tissue/blood vessel image by adding the blood vessel image acquired by the first calculation unit and the soft tissue image acquired by the third calculation unit.

6. The X-ray imaging device according to claim 5, wherein all of the first to third reconstruction units perform a high-frequency emphasis at the time of reconstruction, and which further comprises a filter which performs a low-frequency emphasis for the soft tissue image data acquired by the third calculation unit.

7. The X-ray imaging device according to claim 5, wherein the first reconstruction unit performs a high-frequency emphasis and a low-frequency emphasis at the time of reconstruction, wherein the third reconstruction unit performs a low-frequency emphasis at the time of reconstruction, and wherein the third calculation unit acquires the soft tissue image by adding a tissue image acquired by performing the low-frequency emphasis with the first reconstruction unit and a tissue image acquired by performing the low-frequency emphasis with the first reconstruction unit.

8. An X-ray imaging device comprising:

an X-ray generation unit which emits X-rays to a sample;

an X-ray detection unit which detects the amount of X-rays passing through the sample;

an imaging control unit which two or more times rotate the X-ray generation unit and the X-ray detection unit around the sample as a rotation center and imaging the sample at a plurality of rotation angles different from each other during the rotation; and an image calculation unit which acquires a three-dimensional image of the sample by performing a calculation process including at least a reconstruction to the plurality of two-dimensional images which are acquired by performing imaging during the rotations of the X-ray generation unit and the X-ray detection unit, the image calculation unit including:

a first reconstruction unit which acquires a tissue image of the sample by performing a reconstruction to the two-dimensional images acquired from the sample without a contrast, a second reconstruction unit which acquires a tissue/blood vessel image including tissues and blood vessels of the sample by performing a reconstruction to the two-dimensional images acquired from the sample with a contrast, and an inter-image calculation unit which acquires a three-dimensional soft tissue image, a three-dimensional soft tissue/blood vessel image, and a three-dimensional blood vessel image, by performing an inter-calculation between the tissue image and the tissue/blood vessel image, the inter-image calculation unit further includes including:

a first calculation unit which acquires the blood vessel image from the difference between the tissue image and the tissue/blood vessel image, a projection image unit which acquires a plurality of two-dimensional images by projecting the blood vessel image acquired by the first calculation image, a second calculation unit which acquires a plurality of tissue images from the difference between the two-dimensional images acquired by the projection image unit and the two-dimensional images acquired from the sample with a contrast, a third calculation unit which acquires a plurality of tissue images by adding the tissue images acquired by the second calculation unit and the two-dimensional images acquired from the sample without a contrast, a third reconstruction unit which acquires the soft tissue image by reconstructing the tissue images acquired by the third calculation unit, and a fourth calculation unit which acquires the soft tissue/blood vessel image by adding the blood vessel image acquired by the first calculation unit and the soft tissue image acquired by the third reconstruction unit.

9. An X-ray imaging method comprising:

acquiring a plurality of two-dimensional images by imaging a sample at every rotation of an X-ray generation unit and an X-ray detection unit rotating around the sample as a center by a first angle under conditions of not injecting a contrast agent to the sample and not inserting an instrument to the sample;

acquiring a first reconstruction image not including the instrument by performing a reconstruction to the plurality of two-dimensional images;

acquiring a plurality of two-dimensional images by imaging the sample at every rotation of the X-ray generation unit and the X-ray detection unit rotating around the sample as a center by a second angle deviated from the first angle under conditions of not injecting a contrast agent to the sample and proceeding the insertion of the instrument to the sample;

performing an acquisition of the plurality of two-dimensional images several times with time under conditions of not injecting a contrast agent to the sample and proceeding the insertion of the instrument to the sample;

sequentially acquiring second reconstruction images including the instrument by performing a reconstruction to the plurality of two-dimensional images at every time acquiring the plurality of second two-dimensional images; and sequentially acquiring three-dimensional soft tissue/instrument images in which at least the sample is inserted with the instrument with time, by performing an inter-calculation between the first reconstruction image and the second reconstruction image.

* * * * *